(12) United States Patent
Legrand

(10) Patent No.: US 7,569,078 B2
(45) Date of Patent: Aug. 4, 2009

(54) DYE COMPOSITION COMPRISING AT LEAST ONE CELLULOSE AND PROCESS FOR DYEING KERATIN FIBERS USING THE DYE COMPOSITION

(75) Inventor: Frédéric Legrand, Tokyo (JP)

(73) Assignee: L'Oreal S.A., Paris (FR)

( * ) Notice: Subject to any disclaimer, the term of this patent is extended or adjusted under 35 U.S.C. 154(b) by 130 days.

(21) Appl. No.: 11/394,234

(22) Filed: Mar. 31, 2006

(65) Prior Publication Data
US 2006/0260071 A1    Nov. 23, 2006

Related U.S. Application Data

(60) Provisional application No. 60/681,151, filed on May 16, 2005.

(30) Foreign Application Priority Data
Mar. 31, 2005    (FR) .................................. 05 50842

(51) Int. Cl.
A61Q 5/10    (2006.01)
(52) U.S. Cl. ....................... 8/405; 8/406; 8/407; 8/435; 8/552; 8/554; 8/559
(58) Field of Classification Search ...................... 8/405, 8/406, 407, 435, 552, 554, 559
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmer | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,836,537 A | 9/1974 | Boerwinkle et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,031,307 A | 6/1977 | DeMartino et al. | |
| 4,075,136 A | 2/1978 | Schaper | |
| 4,116,894 A | 9/1978 | Lentz et al. | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |

(Continued)

FOREIGN PATENT DOCUMENTS

| | | |
|---|---|---|
| DE | 30 30 119 | 11/1987 |
| DE | 38 34 142 | 4/1990 |
| DE | 41 27 230 | 2/1993 |
| DE | 41 03 292 | 2/1994 |
| DE | 101 32 915 | 1/2003 |
| EP | 0 080 976 B1 | 6/1983 |
| EP | 0 122 324 B1 | 10/1984 |
| EP | 0 337 354 B1 | 10/1989 |
| EP | 0 412 706 A2 | 2/1991 |
| EP | 0 714 954 B1 | 6/1996 |

(Continued)

OTHER PUBLICATIONS

English language abstract of non-English document EP 0 080 976, (Jun. 1983).
European Search Report for EP 06 11 1856 (European counterpart application to U.S. Appl. No. 11/394,234, the present application), dated Jul. 19, 2006.

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclosed herein is a dye composition comprising water in an amount greater than or equal to 40% by weight, relative to the total weight of the composition, and a process for dyeing keratin fibers, for example, human keratin fibers, using such a composition. This dye composition additionally comprise at least one dye chosen from oxidation dye precursors and direct dyes; at least one surfactant chosen from nonionic surfactants and anionic surfactants; at least one nonionic cellulose modified with at least one group comprising saturated and unsaturated, linear and branched $C_6$-$C_{30}$ hydrocarbon chains, and at least one cationic associative polymer. Also disclosed herein is a multi-compartment device or kit separately comprising the dye composition and an oxidizing composition.

27 Claims, No Drawings

U.S. PATENT DOCUMENTS

| | | | |
|---|---|---|---|
| 4,579,732 A | 4/1986 | Grollier et al. |
| 4,591,610 A | 5/1986 | Grollier |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,761,273 A | 8/1988 | Grollier et al. |
| 4,777,040 A | 10/1988 | Grollier et al. |
| 4,803,221 A | 2/1989 | Bair |
| 4,839,166 A | 6/1989 | Grollier et al. |
| 4,919,923 A | 4/1990 | Hoeffkes et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,057,311 A | 10/1991 | Kamegai et al. |
| 5,089,252 A | 2/1992 | Grollier et al. |
| 5,139,037 A | 8/1992 | Grollier et al. |
| 5,196,189 A | 3/1993 | Jacquet et al. |
| 5,480,459 A | 1/1996 | Mager et al. |
| 5,494,489 A | 2/1996 | Akram et al. |
| 5,708,151 A | 1/1998 | Mockli |
| 5,792,221 A | 8/1998 | Lagrange et al. |
| 5,958,392 A | 9/1999 | Grollier et al. |
| 5,990,233 A | 11/1999 | Barron et al. |
| 6,106,578 A | 8/2000 | Jones |
| 6,436,151 B2 * | 8/2002 | Cottard et al. ............ 8/406 |
| 6,540,791 B1 | 4/2003 | Dias |
| 6,613,315 B1 | 9/2003 | Dupuis |
| 6,800,098 B1 | 10/2004 | Allard et al. |
| 6,824,570 B2 | 11/2004 | Vidal et al. |
| 6,881,230 B2 | 4/2005 | Vidal |
| 6,884,265 B2 | 4/2005 | Vidal et al. |
| 6,884,267 B2 | 4/2005 | Vidal et al. |
| 6,893,471 B2 | 5/2005 | Vidal |
| 7,001,436 B2 | 2/2006 | Vidal et al. |
| 7,022,143 B2 | 4/2006 | Vidal et al. |
| 7,060,110 B2 | 6/2006 | Vidal et al. |
| 7,077,873 B2 | 7/2006 | David et al. |
| 7,261,743 B2 | 8/2007 | Plos et al. |
| 2001/0023514 A1 | 9/2001 | Cottard et al. |
| 2002/0095732 A1 | 7/2002 | Kravtchenko et al. |
| 2003/0084516 A9 | 5/2003 | Kravtchenko et al. |
| 2003/0106169 A1 | 6/2003 | Vidal et al. |
| 2003/0124079 A1 | 7/2003 | Mougin et al. |
| 2003/0192134 A1 | 10/2003 | Desenne et al. |
| 2004/0047821 A1 | 3/2004 | Maubru et al. |
| 2004/0060126 A1 | 4/2004 | Cottard et al. |
| 2004/0093675 A1 | 5/2004 | Vidal et al. |
| 2004/0093676 A1 | 5/2004 | Vidal et al. |
| 2004/0098815 A1 | 5/2004 | Schmenger et al. |
| 2004/0107513 A1 | 6/2004 | Vidal et al. |
| 2004/0127692 A1 | 7/2004 | David et al. |
| 2004/0133995 A1 | 7/2004 | Cottard et al. |
| 2004/0141943 A1 | 7/2004 | Mougin et al. |
| 2004/0143911 A1 | 7/2004 | Vidal |
| 2004/0168263 A1 | 9/2004 | Vidal |
| 2004/0172771 A1 | 9/2004 | Cottard et al. |
| 2004/0180030 A1 | 9/2004 | Maubru |
| 2004/0187225 A1 | 9/2004 | Vidal et al. |
| 2004/0200009 A1 | 10/2004 | Vidal |
| 2004/0205902 A1 | 10/2004 | Cottard et al. |
| 2004/0216246 A1 | 11/2004 | Cotteret et al. |
| 2004/0244123 A1 | 12/2004 | Vidal et al. |
| 2005/0000039 A1 | 1/2005 | Audosset |
| 2005/0039268 A1 | 2/2005 | Plos et al. |
| 2005/0081311 A1 | 4/2005 | Schmenger et al. |

FOREIGN PATENT DOCUMENTS

| | | | |
|---|---|---|---|
| EP | 0 824 914 B1 | 2/1998 |
| EP | 0 825 200 A1 | 2/1998 |
| EP | 1 048 289 | 11/2000 |
| EP | 1 142 555 | 10/2001 |
| EP | 1 174 450 A1 | 1/2002 |
| EP | 1 232 739 | 8/2002 |
| EP | 1 413 287 | 4/2004 |
| EP | 1 426 032 | 6/2004 |
| EP | 1 426 039 | 6/2004 |
| EP | 1 428 506 | 6/2004 |
| EP | 1 473 025 | 11/2004 |
| EP | 1 518 547 | 3/2005 |
| FR | 1 400 366 A | 5/1965 |
| FR | 1 492 597 A | 8/1967 |
| FR | 1 583 363 A | 10/1969 |
| FR | 2 077 143 A5 | 10/1971 |
| FR | 2 080 759 A1 | 11/1971 |
| FR | 2 162 025 A1 | 7/1973 |
| FR | 2 190 406 A2 | 2/1974 |
| FR | 2 252 840 A1 | 6/1975 |
| FR | 2 270 846 A1 | 12/1975 |
| FR | 2 280 361 A2 | 2/1976 |
| FR | 2 316 271 A1 | 1/1977 |
| FR | 2 320 330 A1 | 3/1977 |
| FR | 2 336 434 A1 | 7/1977 |
| FR | 2 368 508 A2 | 5/1978 |
| FR | 2 383 660 A1 | 10/1978 |
| FR | 2 393 573 A1 | 1/1979 |
| FR | 2 413 907 A1 | 8/1979 |
| FR | 2 470 596 A1 | 6/1981 |
| FR | 2 505 348 | 11/1982 |
| FR | 2 519 863 A1 | 7/1983 |
| FR | 2 542 997 A1 | 9/1984 |
| FR | 2 598 611 A1 | 11/1987 |
| FR | 2 692 572 A1 | 12/1993 |
| FR | 2 717 076 | 9/1995 |
| FR | 2 795 312 | 12/2000 |
| FR | 2 803 195 | 7/2001 |
| FR | 2 807 650 A1 | 10/2001 |
| FR | 2 822 693 A1 | 10/2002 |
| FR | 2 822 694 A1 | 10/2002 |
| FR | 2 822 696 A1 | 10/2002 |
| FR | 2 822 698 A1 | 10/2002 |
| FR | 2 825 625 A1 | 12/2002 |
| FR | 2 825 702 A1 | 12/2002 |
| FR | 2 829 926 A1 | 3/2003 |
| FR | 2 833 833 A1 | 6/2003 |
| FR | 2 844 269 A1 | 3/2004 |
| GB | 1021400 | 3/1966 |
| GB | 1 331 819 | 9/1973 |
| GB | 1 347 051 | 2/1974 |
| GB | 1 479 786 | 7/1977 |
| GB | 1546809 | 5/1979 |
| WO | WO 95/01772 A1 | 1/1995 |
| WO | WO 95/15144 A1 | 6/1995 |
| WO | WO 99/40893 A1 | 8/1999 |
| WO | WO 00/68282 A1 | 11/2000 |
| WO | WO 02/30370 | 4/2002 |
| WO | WO 02/45674 A1 | 6/2002 |
| WO | WO 02/074271 | 9/2002 |
| WO | WO 02/078660 A1 | 10/2002 |
| WO | WO 02/100369 A2 | 12/2002 |
| WO | WO 02/100834 A1 | 12/2002 |
| WO | WO 2004/019895 | 3/2004 |

OTHER PUBLICATIONS

French Search Report for FR 0550842 (Priority Application for U.S. Appl. No. 11/394,234, the present application), dated Feb. 15, 2006.

Bruin "Hydrophobically Modified Cellulose Ether for Personal Care." SOFW-Journal Seifen, Oele, Fette, Wachse, Verlag fur Chemische Industri, Augsburg, DE, vol. 120, No. 15, Nov. 30, 1994, pp. 944-946, 948, XP000483287, ISSN: 0942-7694.

Copending U.S. Appl. No. 11/393,694, filed Mar. 31, 2006.

Copending U.S. Appl. No. 11/393,696, filed Mar. 31, 2006.
Copending U.S. Appl. No. 11/393,698, filed Mar. 31, 2006.
Copending U.S. Appl. No. 11/393,700, filed Mar. 31, 2006.
Copending U.S. Appl. No. 11/393,701, filed Mar. 31, 2006.
English language Derwent Abstract of DE 101 32 915, dated Jan. 31, 2003.
English language Derwent Abstract of DE 30 30 119, dated Nov. 19, 1987.
English language Derwent Abstract of DE 38 34 142, dated Apr. 12, 1990.
English language Derwent Abstract of DE 41 03 292, dated Feb. 10, 1994.
English language Derwent Abstract of DE 41 27 230, dated Feb. 18, 1993.
English language Derwent Abstract of EP 1 048 289, dated Nov. 2, 2000.
English language Derwent Abstract of EP 1 232 739, dated Aug. 21, 2002.
English language Derwent Abstract of EP 1 518 547, dated Mar. 30, 2005.
English language Derwent Abstract of FR 2 795 312, dated Dec. 29, 2000.
European Search Report for EP 06 11 1858 (corresponding European counterpart application to U.S. Appl. No. 11/393,698, dated Jul. 19, 2006, Examiner Loloiu.
European Search Report for EP 06 11 1860 (corresponding European counterpart applciation to U.S. Appl. No. 11/393,701, dated Jul. 18, 2006, Examiner Loloiu.
European Search Report for EP 06111861.8 (corresponding European counterpart application to U.S. Appl. No. 11/393,694, dated Jun. 14, 2006, Examiner Loloiu.
French Search Report for FR 05/50835 for U.S. Appl. No. 11/393,700, dated Nov. 3, 2005, Examiner Loloiu.
French Search Report for FR 05/50837 for U.S. Appl. No. 11/393,694, dated Nov. 10, 2005, Examiner Loloiu.
French Search Report for FR 05/50838 for U.S. Appl. No. 11/393,698, dated Nov. 4, 2005, Examiner Loloiu.
French Search Report for FR 05/50839 for U.S. Appl. No. 11/393,701, dated Nov. 9, 2005, Examiner Loloiu.
French Search Report for FR 05/50841 for U.S. Appl. No. 11/393,696, dated Feb. 14, 2006, Examiner Loloiu.
G. Fonnum, J. Bakke and Fk. Hansen - Colloid Polym. Sci. 271, 380-389 (1993).
Office Action mailed Jan. 7, 2008, in co-pending U.S. Appl. No. 11/393,694, Examiner E. Elhilo.
Office Action mailed Jan. 7, 2008, in co-pending U.S. Appl. No. 11/393,696, Examiner E. Elhilo.
Office Action mailed Jan. 7, 2008, in co-pending U.S. Appl. No. 11/393,698, Examiner E. Elhilo.
Office Action mailed Jan. 7, 2008, in co-pending U.S. Appl. No. 11/393,700, Examiner E. Elhilo.
Office Action mailed Jan. 7, 2008, in co-pending U.S. Appl. No. 11/393,701, Examiner E. Elhilo.
Office Action mailed Jun. 13, 2008, in co-pending U.S. Appl. No. 11/393,698, Examiner E. Elhilo.
Office Action mailed Jun. 18, 2008, in co-pending U.S. Appl. No. 11/393,700, Examiner E. Elhilo.
Office Action mailed Jun. 23, 2008, in co-pending U.S. Appl. No. 11/393,694, Examiner E. Elhilo.
Office Action mailed Jun. 27, 2008, in co-pending U.S. Appl. No. 11/393,701, Examiner E. Elhilo.
Office Action mailed Oct. 22, 2008, in co-pending U.S. Appl. No. 11/393,698, Examiner E. Elhilo.

* cited by examiner

DYE COMPOSITION COMPRISING AT LEAST ONE CELLULOSE AND PROCESS FOR DYEING KERATIN FIBERS USING THE DYE COMPOSITION

This application claims benefit of U.S. Provisional Application No. 60/681,151, filed May 16, 2005, the contents of which are incorporated herein by reference. This application also claims benefit of priority under 35 U.S.C. § 119 to French Patent Application No. FR 05 50842, filed Mar. 31, 2005, the contents of which are also incorporated herein by reference.

Disclosed herein is a dye composition comprising at least one dye, at least one surfactant chosen from nonionic surfactants and anionic surfactants, at least one amphiphilic cellulose, at least one cationic associative polymer, wherein the dye composition comprises water in an amount greater than or equal to 40% by weight, relative to the total weight of the composition. Also disclosed herein is a process for dyeing keratin fibers, for example, human keratin fibers, using such a composition. Further disclosed herein is a multicompartment device or kit comprising the dye composition and an oxidizing composition comprising at least one oxidizing agent.

There are essentially two types of dyeing of keratin fibers, for example,human keratin fibers, such as the hair.

The first, called oxidation dyeing or permanent dyeing, involves using oxidation dye precursors, which are faintly colored or colorless substances. When they are exposed to an oxidizing agent, these compounds produce, through a process of oxidative condensation taking place inside the fiber, colored substances which remain trapped inside the fiber.

The second, known as direct or semi-permanent dyeing, is obtained using colored and dye compounds having affinity with the keratin fibers to which they are applied. This type of dyeing does not require the use of an oxidizing agent to develop the color, although it is not impossible for this type of agent to be present during the process. The latter case is then referred to as direct color lightening.

The dye compositions of known in the prior art are, in the majority of cases, in the form of liquids, gels or creams which are, if necessary, mixed, before applying to the fibers, with an oxidizing composition.

The dye compositions aremay be relatively rich in raw materials, among which are usually fatty substances, surfactants and/or polymers. These compositions are typically formulated such that they exhibit spreading properties and textures which are easy to work with in order to allow easy and rapid application to the fibers, while being sufficiently thick so as not to run outside of the areas which it is desired to dye. Furthermore, these compositions should remain stable during the leave-in time on the fibers and should be easy to remove on rinsing once the color has been obtained.

Large quantities of raw materials may affect the dyeing performance of such compositions. It is thus possible to observe a less favorable kinetics, a reduced intensity of the shade obtained, a less satisfactory homogeneity of the color from one fiber to another and/or according to the position on the fiber (root/end), and the like.

Disclosed herein are dye compositions which avoid at least one of the abovementioned disadvantages of current dye compositions, while preserving at least one of the properties mentioned above.

Disclosed herein are dye compositions comprising, in a medium appropriate for dyeing keratin fibers:
  at least one dye chosen from oxidation dye precursors and direct dyes;
  at least one surfactant chosen from nonionic surfactants and anionic surfactants;
  at least one nonionic cellulose modified with at least one group chosen from saturated and unsaturated, linear and branched $C_6$-$C_{30}$ hydrocarbon chains; and
  at least one cationic associative polymer;
    wherein the composition comprises water in an amount greater than or equal to 40% by weight relative to the total weight of the composition.

Also disclosed herein is a process for dyeing keratin fibers using such a composition, and, in some embodiments, in the presence of an oxidizing composition.

Further disclosed herein is a device comprising a first compartment comprising a dye composition according to the disclosure and a second compartment comprising an oxidizing composition.

The composition according to the disclosure may cause less deterioration of the dyeing properties and may make it possible to obtain colors which are more intense, more homogeneous and more chromatic, while conferring good cosmetic properties on the treated fibers and while limiting their deterioration.

The compositions disclosed herein may have an ideal texture for use in dyeing human keratin fibers, for example, the hair. They may be unctuous, sufficiently thick for rapid and easy application, with good removal upon rinsing, without as a result running outside the areas of the hair which it is desired to treat.

Other characteristics and benefits of the present disclosure will emerge more clearly upon reading the description and the example which follow.

In the text below, and unless otherwise stated, it is specified that the limits of the ranges of values are included in these ranges.

When reference is made herein to a compound with a fatty chain, this chain is a saturated or unsaturated, linear or branched hydrocarbon chain comprising from 8 to 30 carbon atoms, for example, from 10 to 24 carbon atoms.

As discussed above, the composition disclosed herein present is appropriate for dyeing keratin fibers, for example, human keratin fibers, further, for example, the hair.

As used herein, the expression "at least one" is understood to mean one or more individual compounds, and also mixtures thereof.

The dye composition disclosed herein comprises water in an amount greater than or equal to 40% by weight, relative to the total weight of the dye composition.

According to one embodiment, the dye composition disclosed herein comprises water in an amount greater than or equal to 45% by weight, relative to the total weight of the dye composition.

According to another embodiment, the dye composition disclosed herein comprises water in an amount greater than or equal to 50% by weight, relative to the total weight of the dye composition.

The composition disclosed herein comprises at least one surfactant chosen from nonionic surfactants and anionic surfactants.

In one embodiment, the nonionic surfactant(s) can be chosen from:
  oxyalkylenated or glycerolated fatty alcohols;
  oxyalkylenated alkylphenols whose alkyl chain is $C_8$-$C_{18}$;
  oxyalkylenated or glycerolated fatty amides;
  oxyalkylenated vegetable oils;
  optionally oxyalkylenated $C_6$-$C_{30}$ acid esters of sorbitan;
  optionally oxyalkylenated fatty acid esters of sucrose;
  fatty acid esters of polyethylene glycol;
  ($C_6$-$C_{30}$)alkyl polyglycosides;
  N—($C_6$-$C_{30}$)alkylglucamine derivatives;

amine oxides such as $(C_{10}-C_{14})$alkylamine oxides or N-acylaminopropylmorpholine oxides;

copolymers of propylene and ethylene oxide;

and mixtures thereof.

In at least one embodiment, the mean number of oxyalkylenated units may range from 2 to 150 units. In at least one further embodiment, they are oxyethylenated or oxypropylenated units, or mixtures thereof.

The glycerolated surfactants may comprise on average 1 to 20 glycerol groups, for example, 1.5 to 5.

According to one embodiment, the composition comprises at least one nonionic surfactant chosen from oxyalkylenated or glycerolated $C_6-C_{30}$ alcohols.

The at least one anionic surfactant may be chosen from:

$(C_6-C_{30})$alkyl sulphates, $(C_6-C_{30})$alkyl ether sulphates, $(C_6-C_{30})$alkyl amidoether sulphates, alkyl aryl polyether sulphates, monoglyceride sulphates;

$(C_6-C_{30})$alkyl sulphonates, $(C_6-C_{30})$alkyl amide sulphonates, $(C_6-C_{30})$alkyl aryl sulphonates, α-olefin sulphonates, paraffin sulphonates;

$(C_6-C_{30})$alkyl phosphates;

$(C_6-C_{30})$alkyl sulphosuccinates, $(C_6-C_{30})$alkyl ether sulphosuccinates, $(C_6-C_{30})$alkyl amide sulphosuccinates;

$(C_6-C_{30})$alkyl sulphoacetates;

$(C_6-C_{24})$acyl sarcosinates;

$(C_6-C_{24})$acyl glutamates;

$(C_6-C_{30})$alkyl polyglycoside carboxylic ethers; $(C_6-C_{30})$ alkyl polyglycoside sulphosuccinates;

$(C_6-C_{30})$alkyl sulphosuccinamates;

$(C_6-C_{24})$acyl isethionates;

N—$(C_6-C_{24})$acyltaurates;

salts of fatty acids;

$(C_8-C_{20})$acyl lactylates;

salts of $(C_6-C_{30})$alkyl D-galactoside uronic acids;

salts of polyoxyalkylenated $(C_6-C_{30})$alkyl ether carboxylic acids, of polyoxyalkylenated $(C_6-C_{30})$alkyl aryl ether carboxylic acids and of polyoxyalkylenated $(C_6-C_{30})$ alkyl amidoether carboxylic acids;

and mixtures thereof.

In at least one embodiment, the anionic surfactants may be in the form of salts in the composition disclosed herein, for example, salts of alkali metals, for instance sodium; salts of alkaline-earth metals, for instance magnesium; ammonium salts; amine salts; and amino alcohol salts. Depending on the conditions, the anionic surfactants may also be in the acid form thereof.

It should be noted that the alkyl or acyl radicals of these various compounds may comprise, for example, from 12 to 20 carbon atoms. In at least one embodiment, the aryl radical is chosen from a phenyl groups and benzyl groups.

Furthermore, the polyoxyalkylenated anionic surfactants may comprise from 2 to 50 alkylene, for example, ethylene, oxide groups.

According to one embodiment, the anionic surfactant is chosen from the salts of fatty acids.

In at least one embodiment the at least one surfactant chosen from nonionic and anionic surfactants is present in an amount ranging from 0.01% to 50% by weight, such as from 0.5% to 40% by weight, relative to the total weight of the composition.

The composition disclosed herein additionally comprises at least one nonionic cellulose modified with at least one group chosen from saturated and unsaturated, linear and branched $C_6-C_{30}$ hydrocarbon chains.

In one embodiment, the modified nonionic cellulose is chosen from hydroxy$(C_2-C_3)$alkylcelluloses modified with at least one group chosen from saturated and unsaturated, linear and branched $C_6-C_{30}$ hydrocarbon chains, such as for example $C_6-C_{30}$, for example, $C_8-C_{22}$, alkyl, aralkyl or alkylaryl chains.

Also suitable are the hydroxy$(C_2-C_3)$alkylcelluloses modified with polyalkylene glycol alkylphenol ether groups.

As examples of such celluloses, there may be mentioned, with no limitation being implied, modified hydroxyethylcelluloses such as the compounds Natrosol Plus Grade 330 CS 15 bearing $C_{16}$ alkyl chains (marketed by the company Aqualon); Bermocoll EHM 100 (marketed by the company Berol Nobel); Amercell Polymer HM1500 (hydroxyethylcellulose modified with a polyethylene glycol (15) nonylphenol ether—marketed by the company Amerchol).

As discussed above, the composition disclosed herein comprises at least one cationic associative polymer.

The at least one cationic associative polymer is characterized by the presence of hydrophilic regions which bring about the solubility in water, and hydrophobic regions through which the polymers, in an aqueous medium, assemble together or with the hydrophobic parts of other molecules. Such polymers are also capable, in an aqueous medium, of reversibly combining with each other or with other molecules.

In at least one embodiment, the at least one cationic associative polymer may be chosen from amphiphilic polymers comprising at least one fatty chain.

As used herein, "polymer" means compounds exhibiting, in their structure, the repeat of at least one linkage other than the ethylene oxide or propylene oxide or glycerol linkage if this type of linkage is present.

In at least one embodiment, the at least one cationic associative polymer may be chosen from quaternized cellulose derivatives, cationic polyurethanes, cationic polyvinyllactams and cationic acrylic terpolymers, wherein these compounds comprise at least one fatty chain.

Quaternized Cellulose Derivatives

Quaternized cellulose derivatives may, for example, be chosen from:

quaternized celluloses modified with groups comprising at least one fatty chain, such as alkyl, arylalkyl or alkylaryl groups, for example, comprising at least 8 carbon atoms, or mixtures thereof, quaternized hydroxyethylcelluloses modified with groups comprising at least one fatty chain, such as alkyl, arylalkyl or alkylaryl groups, for example, comprising at least 8 carbon atoms, or mixtures thereof.

The alkyl radicals carried by the above quaternized celluloses or hydroxyethylcelluloses may, for example, comprise from 8 to 30 carbon atoms. The aryl radicals may be chosen, for example, from phenyl, benzyl, naphthyl and anthryl groups.

Non-limiting mention may be made, as examples of quaternized alkylhydroxyethylcelluloses with $C_8-C_{30}$ fatty chains, the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) marketed by the company AMERCHOL and the products CRODACEL QM, CRODACEL QL ($C_{12}$ alkyl) and CRODACEL QS ($C_{18}$ alkyl) marketed by the company CRODA.

Cationic Polyurethanes

In at least one embodiment, the at least one cationic associative polyurethane may be chosen from compounds of general formula (Ia):

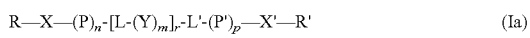

(Ia)

wherein:

R and R', which may be identical or different, are each chosen from hydrophobic groups and hydrogen atoms;

X and X', which may be identical or different, are each chosen from groups comprising an amine functional group carrying or otherwise a hydrophobic group, or alternatively the group L";

L, L' and L", which may be identical or different, are each chosen from groups derived from a diisocyanate;

P and P', which may be identical or different, are each chosen from groups comprising an amine functional group carrying or otherwise a hydrophobic group;

Y is chosen from hydrophilic groups;

r is an integer ranging from 1 to 100, for example, from 1 to 50 and further, for example, from 1 to 25;

n, m and p, which may be identical or different, are each chosen from numbers ranging from 0 to 1,000;

wherein the molecule comprises at least one protonated or quaternized amine functional group and at least one hydrophobic group.

These compounds have been described in European Patent Application No. EP1 174 450.

In at least one embodiment, the only hydrophobic groups are the groups R and R' at the chain ends.

In at least one other embodiment:

R and R', which may be identical or different, are each chosen from hydrophobic groups, X, X' which may be identical or different, are each chosen from L", n and p, which may be identical or different, are each chosen from numbers ranging from 1 to 1000, and L, L', L", P, P', Y and m have the meaning disclosed above.

In at least one further embodiment:

R and R', which may be identical or different, are each chosen from hydrophobic groups, X, X', which may be identical or different, are each chosen from L", n and p are equal to 0, and L, L', L", Y and m have the meaning disclosed above.

When n and p are equal to 0, these polymers do not comprise units derived from a monomer comprising an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents comprising a hydrophobic group, that is to say compounds of the RQ or R'Q type, wherein R and R' are as defined above and Q is chosen from a leaving group such as a halide, a sulphate and the like.

In at least one further embodiment:

R and R', which may be identical or different, are each chosen from hydrophobic groups, X and X', which may be identical or different, are each chosen from quaternary amines, n and p are equal to zero, and L, L', Y and m have the meaning disclosed above.

The number-average molecular mass of the cationic amphiphilic polyurethanes may range from 400 to 500,000, for example, from 1,000 to 400,000, and further, for example, from 1,000 to 300,000.

As used herein, "hydrophobic group" is understood to mean a radical or polymer comprising a saturated or unsaturated, linear or branched hydrocarbon chain comprising at least one heteroatom such as P, O, N, S or radicals comprising a perfluorinated or silicone chain. When the hydrophobic group is chosen from a hydrocarbon radical, the hydrophobic group comprises at least 10 carbon atoms, such as from 10 to 30 carbon atoms, for example, from 12 to 30 carbon atoms, and further, for example, from 18 to 30 carbon atoms.

In one embodiment, the hydrocarbon group may be derived from a monofunctional compound.

In another embodiment, the hydrophobic group may be derived from a fatty alcohol such as stearyl alcohol, dodecyl alcohol, decyl alcohol. It may also be chosen from hydrocarbon polymers such as polybutadiene.

When X and/or X' are chosen from groups comprising a tertiary or quaternary amine, X and/or X' may be chosen from:

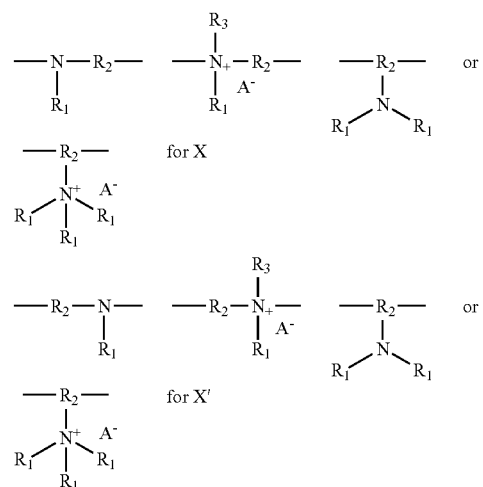

wherein:

$R_2$ is chosen from linear or branched alkylene radicals comprising from 1 to 20 carbon atoms, comprising a saturated or unsaturated ring, and arylene radicals, wherein at least one of the carbon atoms is optionally replaced by a heteroatom chosen from N, S, O, P;

$R_1$ and $R_3$, which may be identical or different, are chosen from linear and branched, $C_1$-$C_{30}$ alkyl and alkenyl radicals, aryl radicals, wherein at least one of the carbon atoms is optionally replaced by a heteroatom chosen from N, S, O, P;

$A^-$ is a physiologically acceptable counterion.

The groups L, L' and L" are chosen from:

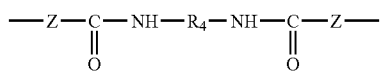

wherein:

Z is chosen from —O—, —S— or —NH—; and $R_4$ is chosen from linear or branched alkylene radicals having from 1 to 20 carbon atoms, comprising a saturated or unsaturated ring; arylene radicals, wherein at least one of the carbon atoms may be optionally replaced by a heteroatom chosen from N, S, O, and P.

The groups P and P', comprising an amine functional group, are chosen from:

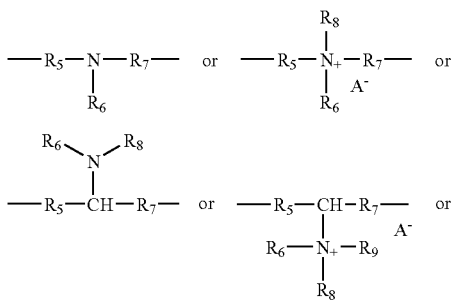

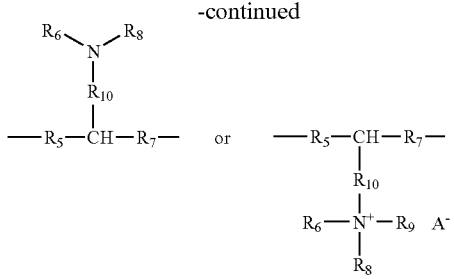

-continued wherein:

$R_5$ and $R_7$ have the same meanings as $R_2$ defined above;

$R_6$, $R_8$ and $R_9$ have the same meanings as $R_1$ and $R_3$ defined above;

$R_{10}$ is chosen from linear and branched alkylene groups, which are optionally unsaturated and which may comprise at least one heteroatom chosen from N, O, S and P, and $A^-$ is a physiologically acceptable counterion.

In Y, "hydrophilic group" understood to mean a polymeric or nonpolymeric water-soluble group.

In one embodiment, Y, when polymers are not involved, may be chosen from ethylene glycol, diethylene glycol and propylene glycol.

In one embodiment, when a hydrophilic polymer is present in the composition disclosed herein, Y may be chosen, for example, from polyethers, sulphonated polyesters, sulphonated polyamides, or a mixture of these polymers. In another embodiment, the hydrophilic compound is a polyether, for example, a polyethylene oxide or a polypropylene oxide.

The hydrophilic group noted Y in formula (Ia) is optional. In one embodiment, the units comprising quaternary or protonated amine functional groups may suffice to provide the solubility or water-dispersibility necessary for this type of polymer in an aqueous solution.

Although the presence of a hydrophilic group Y is optional, in one embodiment, cationic amphiphilic polyurethanes may comprise group Y.

Said cationic amphiphilic polyurethanes may be water-soluble or water-dispersible.

Cationic Polyvinyllactams

The associative cationic poly(vinyllactam) polymers may be, for example, chosen from:
a) at least one monomer of the vinyllactam or alkylvinyl-lactam type;
b) at least one monomer having the following structures (Ib) or (IIb):

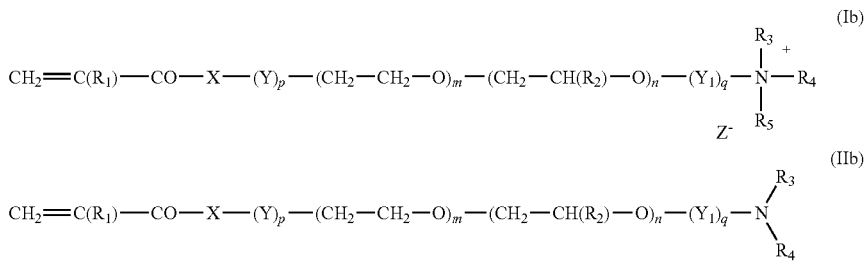

wherein:

X is chosen from oxygen atom and $NR_6$ radicals, $R_1$ and $R_6$, which may be identical or different, are each chosen from hydrogen atoms and linear and branched $C_1$-$C_5$ alkyl radicals, $R_2$ is chosen from linear or branched $C_1$-$C_4$ alkyl radicals, $R_3$, $R_4$ and $R_5$, which may be identical or different, are each chosen from hydrogen atoms, linear and branched $C_1$-$C_{30}$ alkyl radicals and radicals of formula (IIIb):

$$-(Y_2)_r-(CH_2-CH(R_7)-O)_x-R_8 \qquad (IIIb)$$

Y, $Y_1$ and $Y_2$, which may be identical or different, are each chosen from linear and branched $C_2$-$C_{16}$ alkylene radicals, $R_7$ is chosen from hydrogen atoms, linear and branched $C_1$-$C_4$ alkyl radicals and linear and branched $C_1$-$C_4$ hydroxyalkyl radicals, $R_8$ is chosen from hydrogen atoms and linear and branched $C_1$-$C_{30}$ alkyl radicals, p, q and r, which may be identical or different, are each chosen from 0 and 1, m and n, which may be identical or different, are each chosen from integers ranging from 0 to 100, x is chosen from an integer ranging from 1 to 100, Z is chosen from an organic or inorganic acid anion, wherein:
at least one of the substituents $R_3$, $R_4$, $R_5$ or $R_8$ is chosen from a linear or branched $C_8$-$C_{30}$, for example, $C_9$-$C_{30}$, alkyl radicals,
if m or n is different from zero, then q is equal to 1,
if m or n are equal to zero, then p or q is equal to 0.

In one embodiment, the associative cationic poly(vinyllactam)polymers may be crosslinked or noncrosslinked and may also be block polymers.

In another embodiment, the counterion $Z^-$ of the monomers of formula (Ib) is chosen from halide ions, phosphate ions, methosulphate ions, and tosylate ions.

In one embodiment, $R_3$, $R_4$ and $R_5$, which may be identical or different, are each chosen from hydrogen atoms and linear or branched $C_1$-$C_{30}$ alkyl radicals.

In one embodiment, the monomer b) is a monomer of formula (Ib) wherein m and n are equal to zero.

The vinyllactam or alkylvinyllactam monomer may, for example, be chosen from compounds having the structure (IVb):

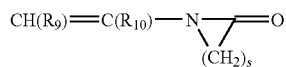

wherein:
s is chosen from an integer ranging from 3 to 6,
$R_9$ is chosen from hydrogen atoms or $C_1$-$C_5$ alkyl radicals,
$R_{10}$ is chosen from a hydrogen atom or $C_1$-$C_5$ alkyl radicals,
provided that at least one of the radicals $R_9$ and $R_{10}$ is chosen from a hydrogen atom.

In one embodiment, the monomer (IVb) is vinylpyrrolidone.

The cationic poly(vinyllactam) polymers may also comprise at least one additional, for example, cationic or nonionic, monomers.

In one embodiment, terpolymers may be used which comprise at least:
a)—one monomer of formula (IVb),
b)—one monomer of formula (Ib) wherein p is 1, q is 0, $R_3$ and $R_4$, which may be identical or different, are each chosen from hydrogen atoms and $C_1$-$C_5$ alkyl radicals and $R_5$ is chosen from $C_8$-$C_{24}$, for example, $C_9$-$C_{24}$, alkyl radicals, and
c)—one monomer of formula (IIb) wherein $R_3$ and $R_4$, which may be identical or different, are each chosen from hydrogen atoms and $C_1$-$C_5$ alkyl radicals.

In another embodiment, the terpolymers are present in the composition disclosed herein in an amount ranging from, by weight, 40 to 95% of monomer (a), 0.1 to 55% of monomer (c) and 0.25 to 50% of monomer (b). Such polymers are described in International Patent Application No. WO-00/68282 which is incorporated herein in full.

In one embodiment, the cationic poly(vinyllactam)polymers are chosen from the terpolymers vinylpyrrolidone/dimethylaminopropylmethacrylamide/dodecyldimethylmethacrylamidopropylammonium tosylate, the terpolymers vinylpyrrolidone/dimethylaminopropylmethacrylamide/cocoyldimethylmethacrylamidopropylammonium tosylate, the terpolymers vinylpyrrolidone/dimethylaminopropylmethacrylamide/-lauryldimethylmethacrylamidopropylammonium tosylate or chloride.

The weight-average molecular mass of the associative cationic poly(vinyllactam) polymers disclosed herein ranges from 500 to $20 \times 10^6$, for example, from 200,000 to $2 \times 10^6$ and further, for example, from 400,000 to 800,000.

Acrylic Terpolymers

In one embodiment, the acrylic terpolymers comprise:
from 5 to 80% by weight, for example, from 15 to 70% by weight and further, for example, from 40 to 70% by weight, of an acrylate monomer (a) chosen from $C_1$-$C_6$ alkyl acrylates and $C_1$-$C_6$ alkyl methacrylates;
from 5 to 80% by weight, for example, from 10 to 70% by weight and further, for example, from 20 to 60% by weight, of a monomer (b) chosen from heterocyclic vinyl compounds comprising at least one nitrogen or sulphur atom, one (meth)acrylamide, one mono- or di-($C_1$-$C_4$)alkylamino($C_1$-$C_4$)alkyl(meth)acrylate and one mono- or di-($C_1$-$C_4$)alkylamino($C_1$-$C_4$)alkyl(meth) acrylamide;
from 0.1 to 30% by weight, for example, from 0.1 to 10% by weight of a monomer (c) chosen from (i) a urethane produced by the reaction between a monoethylenic unsaturated isocyanate and a nonionic surfactant with a $C_1$-$C_4$ alkoxy end; (ii) a 1,2-butylene oxide and 1,2-ethylene oxide block copolymer; (iii) a copolymerizable ethylenic unsaturated surfactant monomer obtained by condensation of a nonionic surfactant with an α,β-ethylenic unsaturated carboxylic acid or its anhydride; (iv) a surfactant monomer chosen from products of reaction of the urea type of a monoethylenic unsaturated monoisocyanate with a nonionic surfactant having an amine functional group; (v) a (meth)allyl ether of formula $CH_2$is $C_1$, $CH_2OA_mB_nA_pR_2$ wherein $R_1$ is chosen from hydrogen atoms and methyl groups, A is chosen from propyleneoxy and butyleneoxy groups, B is chosen from ethyleneoxy, n chosen from a number less than or equal to 200, for example, less than 100, m and p are chosen from a number less than n and $R_2$ is a hydrophobic group of at least 8 carbon atoms, for example, $C_8$-$C_{30}$; and (vi) a nonionic monomer of the urethane type produced by the reaction of a monohydric nonionic surfactant with a monoethylenic unsaturated isocyanate; the percentages by weight of monomers being based on the total weight of the monomers constituting the terpolymer.

In one embodiment, acrylate monomers (a) comprise, for example, C2-C6 alkyl acrylates. Ethyl acrylate may be used in one embodiment.

In one embodiment, monomers (b) may be chosen from N,N-dimethylaminoethyl methacrylate (DMAEMA), N,N-diethylaminoethyl acrylate, N,N-diethylaminoethyl methacrylate, N-t-butylaminoethyl acrylate, N-t-butylaminoethyl methacrylate, N,N-dimethylaminopropylacrylamide, N,N-dimethylaminopropyl-methacrylamide, N,N-diethylaminopropylacrylamide and N,N-diethylaminopropyl-methacrylamide. N,N-dimethylaminoethyl methacrylate may be used in one embodiment.

In one embodiment, monomers (c) are chosen from the copolymerizable ethylenic unsaturated surfactant monomers obtained by condensation of a nonionic surfactant with an α,β-unsaturated carboxylic acid or its anhydride, for example, $C_3$-$C_4$ mono- or dicarboxylic acids or their anhydrides and further, for example, acrylic acid, methacrylic acid, crotonic acid, maleic acid, maleic anhydride and even further, for example, itaconic acid and itaconic anhydride.

In another embodiment, monomers (c) are chosen from the copolymerizable ethylenic unsaturated surfactant monomers obtained by condensation of a nonionic surfactant with itaconic acid. Among the nonionic surfactants, there may be mentioned, for example, alkoxylated $C_{10}$-$C_{30}$ fatty alcohols with 2 to 100, for example, from 5 to 50 moles of alkylene oxide, such as for example ethers of polyethylene glycol and $C_{10}$-$C_{30}$ fatty alcohols and, for example, ethers of polyethylene glycol and cetyl alcohol, called CETETH in the CTFA dictionary, 7th edition, 1997.

Conventional methods for preparing these acrylic terpolymers are known to a person skilled in the art. Such methods include solution polymerization, precipitation polymerization and emulsion polymerization. Terpolymers in accordance with the disclosure and their methods of preparation are described, for example, in European Patent Application Nos. EP-A-0824914 and EP-A-0825200.

In one embodiment, the terpolymer may be chosen from the polymer "STRUCTURE® PLUS" sold by the company NATIONAL STARCH, which comprise polyoxyethylenated $C_{10}$-$C_{30}$ alkyl acrylates, amino(meth)acrylates and itaconate comprising 20 moles of ethylene oxide in the form of an aqueous dispersion comprising 20% of Active Substance.

In addition to these monomers, the terpolymers may contain other monomers which make it possible to crosslink said terpolymers. These monomers are used in fairly low proportions, up to 2% by weight relative to the total weight of the monomers used to prepare the terpolymers. Such crosslinking monomers comprise aromatic monomers bearing several vinyl substituents, alicyclic monomers bearing several vinyl substituents, bifunctional esters of phthalic acid, bifunctional esters of methacrylic acid, multifunctional esters of acrylic acid, N-methylenebisacrylamide and aliphatic monomers bearing several vinyl substituents such as dienes, trienes and tetraenes.

Crosslinking monomers may be, for example, divinylbenzenes, trivinylbenzenes, 1,2,4-trivinylcyclohexane, 1,5-hexadiene, 1,5,9-decatriene, 1,9-decadiene, 1,5-heptadiene, diallyl phthalates, ethylene glycol dimethacrylate, polyethylene glycol dimethacrylates, penta- and tetraacrylates, triallylpentaerythritols, octaallylsucrose, cyclo-paraffins, cycloolefins and N-methylenebisacrylamide.

In one embodiment, the cationic associative polymers are present in an amount ranging from 0.01 to 5% by weight, relative to the total weight of the composition, for example, from 0.05 to 2.5% by weight, and even further, for example, from 0.1 to 1% by weight.

The composition disclosed herein additionally comprises at least one dye chosen from oxidation dye precursors and direct dyes.

The at least one oxidation dye precursor may be chosen from oxidation bases and couplers.

The oxidation bases may be, for example, chosen from the oxidation bases conventionally used for oxidation dyeing, for example, para-phenylenediamines, bisphenylalkylenediamines, para-aminophenols, ortho-aminophenols and heterocyclic bases and their addition salts with an acid or with an alkaline agent.

Among the para-phenylenediamines, there may be mentioned, by way of example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy)pyrrolidine and their addition salts with an acid or with an alkaline agent.

The para-phenylenediamines may, for example, be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethoxy-para-phenylenediamine and their addition salts with an acid or with an alkaline agent.

The bisphenylalkylenediamines may be chosen, for example, from N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methyl-phenyl)ethylenediamine, 1,8-bis(2,5-diaminophenoxy)-3,5-dioxaoctane and their addition salts with an acid or with an alkaline agent.

The para-aminophenols may be chosen, for example, from para-aminophenol, 4-amino-3-methylphenol, 4-amino-3-fluorophenol, 4-amino-3-hydroxy-methylphenol, 4-amino-2-methylphenol, 4-amino-2-hydroxymethylphenol, 4-amino-2-methoxymethylphenol, 4-amino-2-aminomethylphenol, 4-amino-2-(β-hydroxy-ethylaminomethyl)phenol, 4-amino-2-fluorophenol and their addition salts with an acid or with an alkaline agent.

The ortho-aminophenols may be chosen, for example, from 2-aminophenol, 2-amino-5-methylphenol, 2-amino-6-methylphenol, 5-acetamido-2-aminophenol and their addition salts with an acid or with an alkaline agent.

The heterocyclic bases may be chosen, for example, from 2,3-diamino-6-methoxypyridine; pyrimidine derivatives, such as, for example, 2,4,5,6-tetraaminopyrimidine or 4-hydroxy-2,5,6-triaminopyrimidine; and pyrazole derivatives with, for example, 1-N-β-hydroxyethyl-4,5-diaminopyrazole; and their addition salts with an acid or with an alkaline agent.

When used, the at least one oxidation base may be present in an amount ranging from 0.0005 to 12% by weight, relative to the total weight of the composition, for example, from 0.005 to 6% by weight, relative to the total weight of the composition.

The composition may also comprise, combined with at least one oxidation base, at least one coupler so as to modify or enrich with glints the shades obtained.

The at least one coupler may be chosen, for example, from the couplers conventionally used in oxidation dyeing, for example, meta-phenylenediamines, meta-aminophenols, meta-diphenols and heterocyclic couplers and their addition salts with an acid or with an alkaline agent.

In at least one embodiment, the at least one coupler may be chosen from 2-methyl-5-aminophenol, 5-N-(β-hydroxyethyl)amino-2-methylphenol, 3-aminophenol, 2-methyl-5-amino-6-chlorophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2-amino-3-hydroxypyridine, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2- c]-1,2,4-triazole, 6-methylpyrazolo-[1,5-a]benzimidazole and their addition salts with an acid or with an alkaline agent.

When present, the at least one coupler may be present in an amount ranging from 0.0001% to 15% by weight, for example, from 0.005% to 12% by weight, relative to the total weight of the composition. In one embodiment, the at least one coupler may be present in an amount ranging from 0.01% to 10% by weight relative to the total weight of the composition.

The addition salts with an acid may be chosen from the hydrochlorides, the hydrobromides, the sulphates, the citrates, the succinates, the tartrates, the tosylates, the benzenesulphonates, the lactates and the acetates.

The at least one direct dye may be chosen from nonionic, cationic and anionic dyes.

By way of nonlimiting examples, there may be mentioned nitrobenzene dyes, azo, azomethine, methine, tetraazapentamethine, anthraquinone, naphthoquinone, benzoquinone, phenothiazine, indigoid, xanthene, phenanthridine and phthalocyanine dyes, those derived from triarylmethane, and natural dyes, alone or as mixtures.

The at least one direct dye may for example be chosen from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine,
1-amino-2-nitro-4-hydroxy-5-methylbenzene.

The at least one direct dye may also be chosen from the yellow and green-yellow nitrobenzene direct dyes; there may be mentioned, for example, the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nibenzene,
1-(β-hydroxyethyl)amino-2-nitrobenzene,
4-(β-hydroxyethyl)amino-3-nitrobenzamide.

The at least one direct dye may also be chosen from blue or purple nitrobenzene direct dyes such as for example:
1-(β-hydroxyethyl)amino-4-N,N-bis(β-hydroxyethyl)amino-2-nitrobenzene,
1-(γ-hydroxypropyl)amino-4-N,N-bis(β-hydroxyethyl)amino-2-nitrobenzene,
1-(β-hydroxyethyl)amino-4-(N-methyl, N-β-hydroxyethyl)amino-2-nitrobenzene,
1-(β-hydroxyethyl)amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
the 2-nitro-para-phenylenediamines of the following formula:

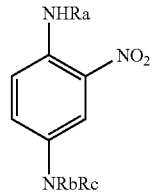

wherein:
Rb is chosen from $C_1$-$C_4$ alkyl radicals, a β-hydroxyethyl or β-hydroxypropyl or γ-hydroxypropyl radicals;
Ra and Rc, which may be identical or different, are each chosen from β-hydroxyethyl, β-hydroxypropyl, γ-hydroxypropyl or β,γ-dihydroxypropyl radicals,
wherein at least one of the radicals Rb, Rc or Ra is chosen from γ-hydroxypropyl radicals and with the proviso that Ra and Rc are not both β-hydroxyethyl radicals when Rb is chosen from γ-hydroxypropyl radicals, such as those described in French Patent No. FR 2 692 572.

Among the azo direct dyes which can be used disclosed herein, non-limiting mention may be made of the cationic azo dyes described in International Patent Application Publication Nos. WO 95/15144, WO 95/01772, WO 02/078 660, WO 02/100 834, and WO 02/100 369; European Patent Application No. EP 714 954, French Patent Application Nos. FR 2 822 696, FR 2 825 702, FR 2 825 625, FR 2 822 698, FR 2 822 693, FR 2 822 694, FR 2 829 926, FR 2 807 650, and FR 2 844 269.

Among these compounds, non limiting mention may be made of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methylsulphate.

The following dyes, described in COLOUR INDEX INTERNATIONAL 3rd edition, may also be mentioned, for example, among the azo direct dyes: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Non-limiting mention may also be made of 1-(4'-aminodiphenylazo)-2-methyl-4bis-(β-hydroxyethyl)aminobenzene and 4-hydroxy-3-(2-methoxyphenylazo)-1-naphthalenesulphonic acid.

The following dyes may be mentioned, for example, among the quinone direct dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and the following compounds:

1-N-methylmorpholiniumpropylamino-4-hydroxyanthraquinone 1-aminopropylamino-4-methylaminoanthraquinone 1-aminopropylaminoanthraquinone 5-β-hydroxyethyl-1,4-diaminoanthraquinone 2-aminoethylaminoanthraquinone 1,4-bis(β,γ-dihydroxypropylamino)anthraquinone.

The following compounds may be mentioned, for example, among the azine dyes:

Basic Blue 17, Basic Red 2.

Among the cationic methine direct dyes, there may also be mentioned, for example, Basic Red 14, Basic Yellow 13 and Basic Yellow 29.

The following compounds may be mentioned, for example, among the triarylmethane dyes which can be used as disclosed herein: Basic Green 1, Acid Blue 9, Basic Violet 3, Basic Violet 14, Basic Blue 7, Acid Violet 49, Basic Blue 26, Acid Blue 7.

The following compounds may be mentioned, for example, among the indoamine dyes which can be used disclosed herein:

2-β-hydroxyethylamino-5-[bis(β-4'-hydroxyethyl)amino]anilino-1,4-benzoquinone

2-β-hydroxyethylamino-5-(2'-methoxy-4'-amino)anilino-1,4-benzoquinone

3-N-(2'-chloro-4'-hydroxy)phenylacetylamino-6-methoxy-1,4-benzoquinoneimine

3-N-(3'-chloro-4'-methylamino)phenylureido-6-methyl-1,4-benzoquinoneimine

3-[4'-N-(ethylcarbamylmethyl)amino]phenylureido-6-methyl-1,4-benzoquinoneimine.

The composition may also comprise natural direct dyes such as lawsone, juglone, alizarin, purpurin, carminic acid, kermesic acid, purpurogallin, procatechaldehyde, indigo, isatin, curcumin, spinulosin and apigenidin. It is also possible to use extracts or decoctions comprising these natural dyes, for example, poultices or extracts based on henna.

The at least one direct dye, when present, may be present in an amount ranging from 0.0005% to 15% by weight relative to the weight of the composition, for example, from 0.005% to 12% by weight relative to the total weight of the composition. In one embodiment, the at least one direct dye may be present in an amount ranging from 0.01% to 5% by weight relative to the total weight of the composition.

According to one embodiment, the composition further comprises at least one fatty substance.

In one embodiment, the at least one fatty substance is chosen from nonoxyalkylenated and nonglycerolated fatty alcohols, nonoxyalkylenated and nonglycerolated fatty acid amides, mono- and polyesters of carboxylic acids, mineral oils, vegetable oils, or mixtures thereof.

Among fatty alcohols, non-limiting mention may be made of $C_8$-$C_{30}$, for example, $C_{10}$-$C_{24}$, even further, for example, $C_{12}$-$C_{24}$, saturated or unsaturated, linear or branched alcohols optionally comprising at least one other hydroxyl group. By way of example, there may be mentioned, oleyl, lauryl, palmityl, myristyl, behenyl, stearyl, linoleyl, linolenyl, capryl and arachidonyl alcohols, or mixtures thereof.

The fatty acid amides may be chosen, for example, from the compounds derived from an alkanolamine and a $C_8$-$C_{30}$ fatty acid. In an embodiment, they are chosen from amides of a $C_2$-$C_{10}$ alkanolamine and a $C_{14}$-$C_{30}$ fatty acid, for example, from the amides of a $C_2$-$C_{10}$ alkanolamine and a $C_{14}$-$C_{22}$ fatty acid.

In one embodiment, the fatty acid amide is chosen from:
oleic acid diethanolamide, such as the amide marketed under the trade name MEXANYL® GT by the company CHIMEX, myristic acid monoethanolamide, such as the amide marketed under the trade name COMPERLAN® MM by the company COGNIS, soyabean fatty acid diethanolamide, such as the amide marketed under the trade name COMPERLAN® VOD by the company COGNIS, stearic acid ethanolamide, such as the amide marketed under the trade name MONAMID® S by the company UNIQEMA, oleic acid monoisopropanolamide, such as the amide marketed under the trade name WITCAMIDE® 61 by the company WITCO, linoleic acid diethanolamide, such as the amide marketed under the trade name PURTON® SFD by the company ZSCHIMMER SCHWARZ, stearic acid monoethanolamide, such as the amide marketed under the trade name MONAMID® 972 by the company ICI/UNIQEMA, behenic acid monoethanolamide, such as the amide marketed under the trade name INCROMIDE® BEM from CRODA, isostearic acid monoisopropanolamide, such as the amide marketed under the trade name WITCAMIDE® SPA by the company WITCO, erucic acid diethanolamide, such as the amide marketed under the trade name erucic acid diethanolamide by the company STEARINERIES DUBOIS, ricinoleic acid monoethanolamide, such as the amide marketed under the trade name ricinoleic monoethanolamide by the company STEARINERIES DUBOIS.

The mono- or polyesters of carboxylic acids, wherein the polyesters are linear or branched, saturated or unsaturated, may, for example, comprise at least one $C_8$-$C_{30}$, for example, $C_{10}$-$C_{24}$, and further, for example, $C_{12}$-$C_{24}$, hydrocarbon chain derived from the acid or alcohol part, and at least one $C_1$-$C_8$, for example, $C_1$-$C_6$, chain. Furthermore, if the carboxylic acid comprises several carboxyl functional groups, these may be, for example, all esterified. Finally, in one embodiment the alcohols are chosen from monofunctional alcohols.

By way of example, non-limiting mention may be made of the esters of oleic, lauric, palmitic, myristic, behenic, stearic, linoleic, linolenic, capric, and arachidonic acids, or mixtures thereof such as the oleopalmitic, oleostearic and palmitostearic mixtures, and the like.

The diisopropyl ester of sebacic acid (diisopropyl sebacate), dioctyl adipate and dicaprylyl maleate may, for example, be mentioned.

In one embodiment, the esters are chosen from those obtained from $C_{12}$-$C_{24}$ acids, for example, acids chosen from carboxyl groups, and saturated, linear or branched $C_3$-$C_6$ monoalcohols.

In one embodiment, the ester is chosen from isopropyl palmitate, and isopropyl myristate, alone or as mixtures.

Paraffin oil is an example of a mineral oil which can be used as a fatty substance in the composition.

The vegetable oils may, for example, be chosen from avocado oil, olive oil or liquid jojoba wax.

In one embodiment, the fatty substance is chosen from oxyalkylenated and nonglycerolated fatty alcohols.

In one embodiment, the total content of fatty substance, if present, is present in an amount of no more than 10% by weight of the dye composition. For example, the total content of fatty substance may be present in an amount ranging from 1 to 9% by weight, relative to the total weight of the composition.

In one embodiment, the surfactant/fatty substance weight ratio is greater than 1.75.

The composition disclosed herein may additionally comprise at least one alkalinizing agent.

Among the alkalinizing agents, there may be mentioned, by way of example, aqueous ammonia, alkali metal carbonates, $C_2$-$C_{10}$ alkanolamines such as mono-, di- and triethanolamines and derivatives thereof, hydroxyalkylamines and oxyethylenated and/or oxypropylenated ethylenediamines, sodium or potassium hydroxides, alkali metal or alkaline-earth metal silicates, and the compounds of the following formula:

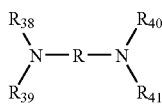

wherein R is a propylene residue optionally substituted with a hydroxyl group or a $C_1$-$C_4$ alkyl radical; $R_{38}$, $R_{39}$, $R_{40}$ and $R_{41}$, which may be identical or different, are each chosen from hydrogen atoms, $C_1$-$C_4$ alkyls and $C_1$-$C_4$ hydroxyalkyl radicals.

In one embodiment, the alkalinizing agent may be chosen from aqueous ammonia, alkanolamines, and combinations of alkanolamines with alkali metal or alkaline-earth metal silicates.

In another embodiment, the composition does not comprise aqueous ammonia as the alkalinizing agent.

The pH of the disclosed composition may, for example, be adjusted using acidifying agents, such as inorganic or organic acids such as hydrochloric acid, orthophosphoric acid, sulphuric acid, carboxylic acids such as acetic acid, tartaric acid, citric acid, lactic acid and sulphonic acids.

For example, the content of basifying and/or acidifying agent is such that the pH of the dye composition ranges from 3 to 12, for example from 4 to 11 and, further for example, from 7 to 11.

The composition disclosed herein may also comprise at least one cationic or amphoteric substantive polymer.

As used herein, the expression "cationic polymer" means any polymer comprising cationic groups and/or groups which can be ionized to cationic groups.

In one embodiment, the at least one cationic polymer may be chosen from those already known per se as improving the cosmetic properties of the hair, for example, those described in European Patent Application No. EP-A-337 354 and in French Patent Nos. FR-2 270 846, 2 383 660, 2 598 611, 2 470 596 and 2 519 863.

The at least one cationic polymer may be chosen from those which comprise units comprising primary, secondary, tertiary and/or quaternary amine groups which may either form part of the main polymer chain, or be carried by a side substituent directly attached thereto.

The cationic polymers used may, for example, have a number-average molecular mass ranging from 500 to $5 \times 10^6$, for example, from $10^3$ to $3 \times 10^6$.

Among the cationic polymers, there may be mentioned, for example, the polymers of the polyamine, polyamino amide and polyquaternary ammonium type, for example, described in French Patent Nos. 2 505 384 or 2 542 997.

Among the cationic polymers, non-limiting mention may be made of:

(1) the homopolymers or copolymers derived from acrylic or methacrylic esters or amides and comprising at least one of the units of the following formulae (I), (II), (III) or (IV):

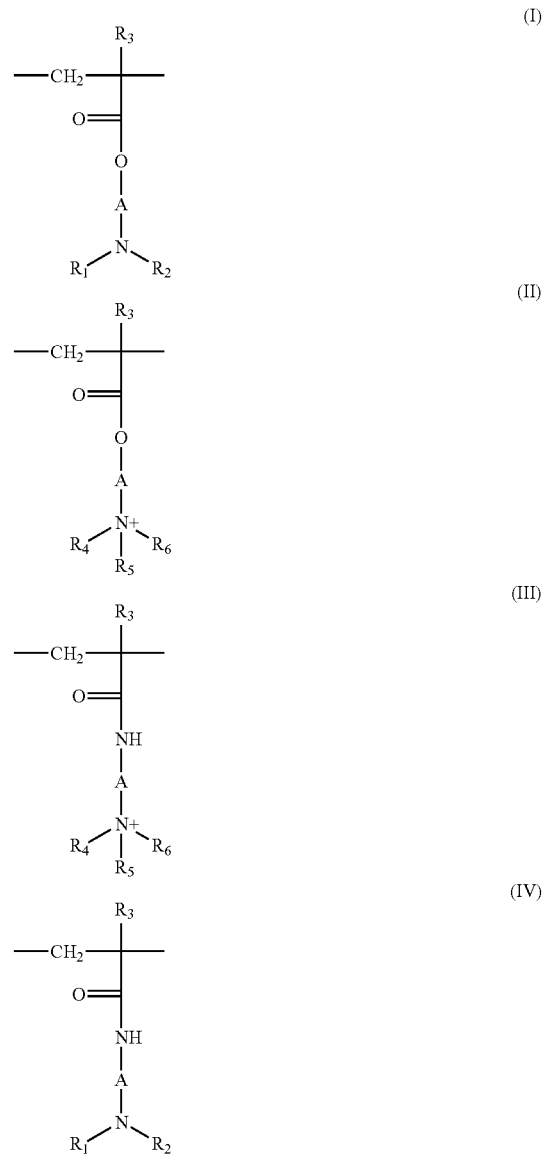

wherein:

$R_3$, which may be identical or different, is chosen from hydrogen atoms and $CH_3$ radicals;

A, which may be identical or different, is chosen from linear or branched alkyl groups of 1 to 6 carbon atoms, for example, 2 or 3 carbon atoms, and hydroxyalkyl groups of 1 to 4 carbon atoms;

$R_4$, $R_5$ and $R_6$, which may be identical or different, are each chosen from benzyl radicals and from alkyl groups comprising from 1 to 18 carbon atoms; for example, from 1 to 6 carbon atoms;

R₁ and R₂, which may be identical or different, are each chosen from hydrogen and from alkyl groups comprising from 1 to 6 carbon atoms, for example methyl or ethyl;

X is an anion derived from an inorganic or organic acid, such as a methosulfate anion or a halide such as chloride or bromide.

The polymers of the family (1) may comprise, for example, at least one unit derived from comonomers which may be chosen from the family of acrylamides, methacrylamides, diacetone acrylamides, acrylamides and methacrylamides substituted on the nitrogen with lower ($C_1$-$C_4$)alkyls, acrylic or methacrylic acids or esters thereof, vinyllactams such as vinylpyrrolidone or vinylcaprolactam, vinyl esters.

Thus, among these polymers of the family (1), non-limiting mention may be made of:

the copolymers of acrylamide and dimethylamino-ethyl methacrylate quaternized with dimethyl sulphate or with a dimethyl halide such as that sold under the name HERCOFLOC by the company HERCULES, the copolymers of acrylamide and methacryloyloxy-ethyl-trimethylammonium chloride described, for example, in European Patent Application No. EP-A-080976 and sold under the name BINA QUAT P 100 by the company CIBA GEIGY, the copolymer of acrylamide and methacryloyloxy-ethyl-trimethylammonium methosulphate sold under the name RETEN by the company HERCULES, the vinylpyrrolidone/dialkylaminoalkyl acrylate or methacrylate copolymers, quaternized or otherwise, such as the products sold under the name "GAFQUAT" by the company ISP such as for example "GAFQUAT 734" or "GAFQUAT 755" or alternatively the products called "COPOLYMER 845, 958 and 937". These polymers are described, for example, in French Patent Nos. 2,077,143 and 2,393,573, the dimethylaminoethyl methacrylate/vinylcapro-lactam/vinylpyrrolidone terpolymers such as the product sold under the name GAFFIX VC 713 by the company ISP, the vinylpyrrolidone/methacrylamidopropyldimethylamine copolymers marketed, for example, under the name STYLEZE CC 10 by ISP, and the quaternized vinylpyrrolidone/dimethyl-aminopropyl methacrylamide copolymers such as the product sold under the name "GAFQUAT HS 100" by the company ISP.

(2) The cellulose ether derivatives comprising quaternary ammonium groups, described in French Patent No. 1,492,597, and, for example, the polymers marketed under the names "JR" (JR 400, JR 125, JR 30M) or "LR" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described, for example, in U.S. Pat. No. 4,131,576, such as hydroxyalkyl celluloses like hydroxymethyl, hydroxyethyl or hydroxypropyl celluloses grafted, for example, with a methacryloylethyltrimethylammonium, methacrylamidopropyltrimethylammonium or dimethyldiallylammonium salt.

The commercialized products corresponding to this definition are, for example, the products sold under the name "Celquat L 200" and "Celquat H 100" by the company National Starch.

(4) The cationic guar gums described, for example, in U.S. Pat. Nos. 3,589,578 and 4,031,307 such as guar gums comprising cationic trialkylammonium groups. Guar gums modified with a 2,3-epoxypropyltri-methylammonium salt (e.g. chloride) are for example used.

Such products are marketed, for example, under the trade names JAGUAR C13 S, JAGUAR C 15, JAGUAR C 17 or JAGUAR C162 by the company MEYHALL.

(5) Polymers comprising piperazinyl units and of alkylene or hydroxyalkylene divalent radicals with straight or branched chains, optionally interrupted by oxygen, sulphur or nitrogen atoms or by aromatic or heterocyclic rings, as well as the oxidation and/or quaternization products of these polymers. Such polymers are described, for example, in French Patent Nos. 2,162,025 and 2,280,361.

(6) Water-soluble polyaminoamides prepared, for example, by polycondensation of an acid compound with a polyamine; these polyaminoamides may be crosslinked with an epihalohydrin, a diepoxide, a dianhydride, an unsaturated dianhydride, a bis-unsaturated derivative, a bishalohydrin, a bisazetidinium, a bishaloacyldiamine, an alkylbishalide or else with an oligomer resulting from the reaction of a difunctional compound which is reactive towards a bishalohydrin, a bisazetidinium, a bishaloacyidiamine, an alkylbishalide, an epihalohydrin, a diepoxide or a bis-unsaturated derivative; the crosslinking agent being employed in proportions ranging from 0.025 to 0.35 mol per amine group of the polyaminoamide; these polyaminoamides may be alkylated or, if they include at least one tertiary amine functional group, quaternized. Such polymers are described, for example, in French Patents 2,252,840 and 2,368,508.

(7) Polyaminoamide derivatives resulting from the condensation of polyalkylenepolyamines with polycarboxylic acids, followed by an alkylation with difunctional agents. There may be mentioned, for example, the adipic acid-dialkylaminohydroxy-alkyldialkylenetriamine polymers wherein the alkyl radical comprises from 1 to 4 carbon atoms and may be, for example, chosen from methyl, ethyl or propyl. Such polymers are described, for example, in French Patent No. 1,583,363.

Among these derivatives there may be mentioned, for example, the adipic acid/dimethyl-aminohydroxypropyl/diethylenetriamine polymers sold under the name "Cartaretine F, F4 or F8" by the company Sandoz.

(8) Polymers obtained by reaction of a polyalkylenepolyamine comprising two primary amine groups and at least one secondary amine group with a dicarboxylic acid chosen from diglycolic acid and saturated aliphatic dicarboxylic acids comprising from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described, for example, in U.S. Pat. Nos. 3,227,615 and 2,961,347.

Polymers of this type are marketed, for example, under the name "Hercosett 57" by the company Hercules Inc. or else under the name of "PD 170" or "Delsette 101" by the company Hercules in the case of the copolymer of adipic acid/epoxypropyl/diethylene-triamine.

(9) Cyclopolymers of alkyldiallylamine or of dialkyldiallylammonium, such as the homopolymers or copolymers comprising, as main constituent of the chain, units corresponding to the formulae (V) or (VI):

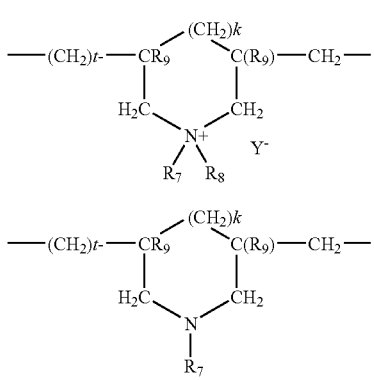

k and t are chosen from 0 or 1, the sum k+t being equal to 1;
$R_9$ is chosen from hydrogen atoms and methyl radicals;
$R_7$ and $R_8$, which may be the same or different, are each chosen from
alkyl groups comprising from 1 to 6 carbon atoms,
hydroxyalkyl groups wherein the alkyl group comprises from 1 to 5 carbon atoms, and
lower ($C_1$-$C_4$) amidoalkyl groups,
or $R_7$ and $R_8$, together with the nitrogen atom to which they are attached, can form heterocyclic groups such as piperidyl or morpholinyl;

For example, $R_7$ and $R_8$, which may be the same or different, are each chosen from alkyl groups having from 1 to 4 carbon atoms; $Y^-$ is chosen from an anion such as bromide, chloride, acetate, borate, citrate, tartrate, bisulfate, bisulfite, sulfate or phosphate. These polymers are described, for example, in French Patent No. 2 080 759 and in its Certificate of Addition 2 190 406.

Among the polymers defined above there may be mentioned, for example, the dimethyldiallylammonium chloride homopolymer sold under the name "Merquat 100" by the company Calgon (and its homologues of low weight-average molecular mass) and the copolymers of diallyl-dimethylammonium chloride and acrylamide marketed under the name "MERQUAT 550".

(10) The quaternary diammonium polymer comprising repeat units corresponding to the formula:

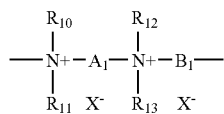

wherein formula (VII):
$R_{10}$, $R_{11}$, $R_{12}$ and $R_{13}$, which may be identical or different, are each chosen from aliphatic, alicyclic or arylaliphatic radicals comprising from 1 to 20 carbon atoms and lower hydroxyalkyl aliphatic radicals, or alternatively $R_{10}$, $R_{11}$, $R_{12}$ and $R_{13}$, together or separately, form, with the nitrogen atoms to which they are attached, heterocyclic rings optionally comprising a second heteroatom other than nitrogen, or alternately $R_{10}$, $R_{11}$, $R_{12}$ and $R_{13}$, which may be identical or different, are each chosen from linear or branched $C_1$-$C_6$ alkyl radicals substituted by a nitrile, ester, acyl, amide or —CO—O—$R_{14}$-D or —CO—NH—$R_{14}$-D group wherein $R_{14}$ is an alkylene and D is chosen from quaternary ammonium groups;

$A_1$ and $B_1$, which may be identical or different, are each chosen from polymethylene groups comprising from 2 to 20 carbon atoms which may be linear or branched, saturated or unsaturated and which may comprise, bonded to or inserted into the main chain, at least one aromatic rings, or at least one oxygen or sulphur atoms or sulphoxide, sulphone, disulphide, amino, alkylamino, hydroxyl, quaternary ammonium, ureido, amide or ester groups, and $X^-$ is chosen from an anion derived from an inorganic or organic acid;

$A_1$, $R_{10}$ and $R_{12}$, with the two nitrogen atoms to which they are attached, may form a piperazine ring; in addition if $A_1$ is chosen from a saturated or unsaturated, linear or branched alkylene or hydroxyalkylene radical, $B_1$ may also be chosen from groups —$(CH_2)_n$—CO-D-OC—$(CH_2)_n$— wherein D is chosen from:

a) a glycol residue of formula: —O—Z—O—, wherein Z is chosen from linear or branched hydrocarbon radicals and groups corresponding to one of the following formulae:

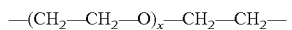

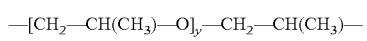

wherein x and y, which may be identical or different, are each chosen from integers ranging from 1 to 4, representing a defined and unique degree of polymerization or x and y are chosen from numbers ranging from 1 to 4 representing a mean degree of polymerization;

b) a disecondary diamine residue such as a piperazine derivative;
c) a diprimary diamine residue of formula: —NH—Y—NH—, wherein Y is chosen from a linear or branched hydrocarbon radicals and —$CH_2$—$CH_2$—S—S—$CH_2$—$CH_2$—;
d) a ureylene group of formula: —NH—CO—NH—.

For example, $X^-$ is chosen from anions such as chloride or bromide.

These polymers may, for example, have a number-average molecular mass ranging from 1,000 to 100,000.

Polymers of this type are described, for example, in French Patent Nos. 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

In one embodiment, it may be possible to use polymers that comprise repeating units corresponding to the following formula (VIII):

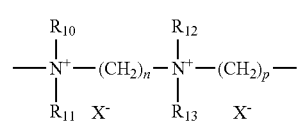

wherein $R_{10}$, $R_{11}$, $R_{12}$ and $R_{13}$, which may be identical or different, are each chosen from alkyl or hydroxyalkyl radicals having from 1 to 4 carbon atoms, n and p are chosen from integers ranging from 2 to 20 and $X^-$ is chosen from an anion derived from an inorganic or organic acid.

(11) The quaternary polyammonium polymers comprising recurring units of formula (IX):

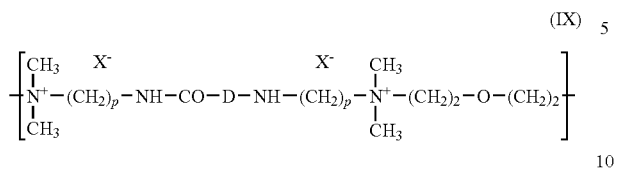

wherein p is chosen from an integer ranging from 1 to 6, D may be a bond or a group—$(CH_2)_r$—CO— wherein r is chosen from number equal to 4 or to 7, $X^-$ is an anion.

Such polymers may be prepared according to the methods described in U.S. Pat. Nos. 4,157,388, 4,702,906, 4,719,282. They are, for example, described in European Patent Application No. EP-A-122 324.

Among these, there may be mentioned, for example the products "Mirapol A 15", "Mirapol AD1", "Mirapol AZ1" and Mirapol 175" sold by the company Miranol.

(12) Quaternary vinylpyrrolidone and vinylimidazole polymers such as, for example, the products marketed under the names Luviquat FC 905, FC 550 and FC 370 by the company B.A.S.F.

(13) Polyamines like the Polyquart H sold by Henkel, referenced under the name of "POLYETHYLENE GLYCOL (15) TALLOW POLYAMINE" in the CTFA dictionary.

(14) The crosslinked polymers of methacryloyloxy($C_1$-$C_4$ alkyl)tri($C_1$-$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, for example, methylenebisacrylamide. For example, it is possible to employ a crosslinked acrylamide/methacryloyloxyethyltrimethylammonium chloride copolymer (20/80 by weight) in the form of a dispersion comprising 50% by weight of said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer comprising approximately 50% by weight of the homopolymer in mineral oil or in a liquid ester. These dispersions are marketed under the names of "SALCARE® SC 95" and "SALCARE® SC 96" by the company ALLIED COLLOIDS.

(15) Other cationic polymers useful herein are are polyalkyleneimines, for example, polyethyleneimines, polymers comprising vinylpyridine or vinylpyridinium units, condensates of polyamines and of epichlorohydrin, quaternary polyureylenes and chitin derivatives.

In at least one embodiment, the cationic polymers may be chosen from the polymers of families (1), (9), (10), (11) and (14) and further, for example, from the polymers comprising repeating units of formulae (W) and (U) below:

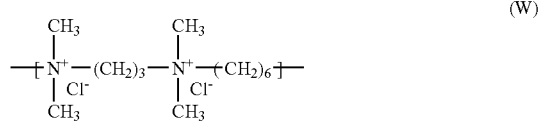

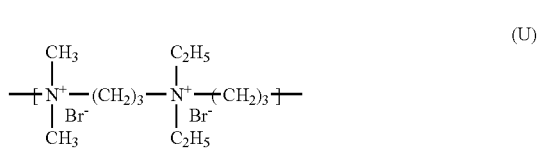

and, for example, those whose molecular weight, determined by gel permeation chromatography, ranges from 9500 to 9900;

and, for example, those whose molecular weight, determined by gel permeation chromatography, is about 1200.

The amphoteric polymers which can be used as disclosed herein, may be chosen from the polymers comprising K and M units distributed randomly in the polymer chain wherein K is chosen from a unit which is derived from a monomer comprising at least one basic nitrogen atom and M is chosen from a unit which is derived from an acidic monomer comprising at least one carboxylic or sulphonic groups or alternatively K and M may be chosen from groups which are derived from zwitterionic monomers of carboxybetaines or of sulphobetaines;

K and M may also be chosen from cationic polymer chains comprising primary, secondary, tertiary or quaternary amine groups, wherein at least one of the amine groups carries a carboxylic or sulphonic group linked via a hydrocarbon radical or alternatively K and M form part of a chain of a polymer with an $\alpha,\beta$-dicarboxylic ethylene unit wherein one of the carboxylic groups has been caused to react with a polyamine comprising at least one primary or secondary amine group.

In at least one embodiment, the amphoteric polymer(s) may be chosen from the following polymers:

(1) The polymers resulting from the copolymerization of a monomer derived from a vinyl compound carrying a carboxylic group such as acrylic acid, methacrylic acid, maleic acid, alpha-chloroacrylic acid, and of a basic monomer derived from a substituted vinyl compound comprising at least one basic atom such as dialkylaminoalkyl methacrylate and acrylate, dialkylaminoalkylmethacrylamide and acrylamide. Such compounds are described in U.S. Pat. No. 3,836,537. Non-limiting mention may also be made of the sodium acrylate/acrylamidopropyltrimethylammonium chloride copolymer sold under the name POLYQUART KE 3033 by the company HENKEL. The vinyl compound may also be a dialkyldiallylammonium salt such as dimethyldiallylammonium chloride. The copolymers of acrylic acid and of the latter monomer are offered under the names MERQUAT 280, MERQUAT 295 and MERQUAT PLUS 3330 by the company CALGON.

(2) The polymers comprising units which are derived from:
  a) at least one monomer chosen from acrylamides or methacrylamides substituted on the nitrogen by an alkyl radical,
  b) at least one acidic comonomer comprising at least one reactive carboxylic group, and
  c) at least one basic comonomer such as esters with primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which may be mentioned, for example, comprise from 2 to 12 carbon atoms, for example, N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen, for example, from acrylic, methacrylic, crotonic, itaconic, maleic and fumaric acids as well as the alkyl monoesters having 1 to 4 carbon atoms of maleic or fumaric anhydrides or acids.

The basic comonomers may be chosen from methacrylates of aminoethyl, butylaminoethyl, N,N'-dimethylaminoethyl, and N-tert-butylaminoethyl.

The copolymers whose CTFA name (4th ed. 1991) is Octylacrylamide/acrylates/butylaminoethylmethacrylate copolymer such as the products sold under the name AMPHOMER or LOVOCRYL 47 by the company NATIONAL STARCH may be used.

(3) The partially or completely alkylated and crosslinked polyaminoamides derived from polyaminoamides of general formula:

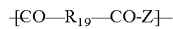
(X)

wherein $R_{19}$ is chosen from
divalent radicals derived from a saturated dicarboxylic acid, mono- or dicarboxylic aliphatic acids with ethylenic double bonds,
esters of a lower alkanol having 1 to 6 carbon atoms of these acids and
radicals which are derived from the addition of any one of said acids with a bis-primary or bis-secondary amine, and
Z is chosen from a radical of a bis-primary, mono- or bis-secondary polyalkylene-polyamine and is chosen from, for example:
a) in an amount of 60 to 100 mol %, the radical

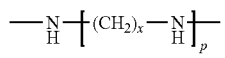
(XI)

where x is 2 and p is chosen from 2 and 3, or alternatively x is 3 and p is 2 this radical being derived from diethylenetriamine, triethylenetetraamine or dipropylenetriamine;
b) in an amount of 0 to 40 mol %, the radical (XI) above, wherein x is 2 and p is 1 and which is derived from ethylenediamine, or the radical which is derived from piperazine:

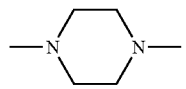

c) in an amount of 0 to 20 mol %, the radical —NH—(CH$_2$)$_6$—NH— which is derived from hexamethylenediamine, these polyaminoamines being crosslinked by adding a bifunctional crosslinking agent chosen from the epihalohydrins, diepoxides, dianhydrides, bis-unsaturated derivatives, by means of 0.025 to 0.35 mol of crosslinking agent per amine group of the polyaminoamide and alkylated by the action of acrylic acid, chloroacetic acid or of an alkanesultone or of their salts.

The saturated carboxylic acids may be, for example, chosen from the acids having 6 to 10 carbon atoms such as adipic, 2,2,4-trimethyladipic and 2,4,4-trimethyladipic acid, terephthalic acid, the acids with an ethylenic double bond such as for example acrylic, methacrylic and itaconic acids.

The alkanesultones used in the alkylation may be, for example, propane or butanesultone, the salts of the alkylating agents may be, for example, the sodium or potassium salts.

(4) The polymers comprising zwitterionic units of formula:

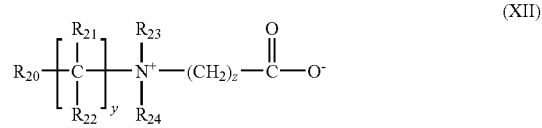
(XII)

wherein
—$R_{20}$ is chosen from polymerizable unsaturated groups such as an acrylate, methacrylate, acrylamide or methacrylamide group,
—y and z are each chosen from an integer ranging from 1 to 3,
—$R_{21}$ and $R_{22}$, which may be identical or different, are each chosen from hydrogen atoms, and methyl, ethyl and propyl radicals,
—$R_{23}$ and $R_{24}$, which may be identical or different, are each chosen from hydrogen atoms and alkyl radicals such that the sum of the carbon atoms in $R_{23}$ and $R_{24}$ does not exceed 10.

The polymers comprising such units may also comprise units derived from nonzwitterionic monomers such as dimethyl or diethylaminoethyl acrylate or methacrylate or alkyl acrylates or methacrylates, acrylamides or methacrylamides or vinyl acetate.

Non-limiting mention may be made of the copolymer of methyl methacrylate/methyl dimethylcarboxymethylammonioethyl methacrylate such as the product sold under the name DIAFORMER Z301 by the company SANDOZ.

(5) The polymers derived from chitosan comprising monomeric units corresponding to the following formulae (XIII), (XIV), (XV):

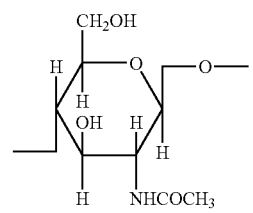
(XIII)

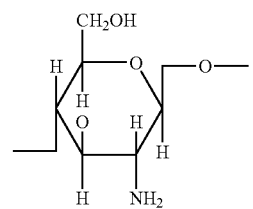
(XIV)

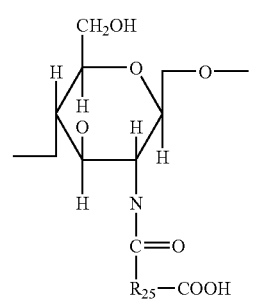
(XV)

the unit (XIII) being present in amounts ranging from 0 to 30%, the unit (XIV) in amounts of 5% to 50% and the unit (XV) in amounts of 30% to 90%, wherein in unit (XV), $R_{25}$ is chosen from radicals of formula:

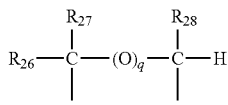

wherein if q is 0, $R_{26}$, $R_{27}$ and $R_{28}$, which may be identical or different, are each chosen from hydrogen atoms, methyl, hydroxyl, acetoxy or amino residues, monoalkylamine residues, dialkylamine residues which are optionally interrupted by at least one nitrogen atom and/or optionally substituted with at least one group chosen from amine, hydroxyl, carboxyl, alkylthio and sulfonic groups, alkylthio residues wherein the alkyl group bears an amino residue, wherein at least one of the radicals $R_{26}$, $R_{27}$ and $R_{28}$ is chosen from a hydrogen atom; or, if q is 1, $R_{26}$, $R_{27}$ and $R_{28}$ are each a hydrogen atom, and also the salts formed by these compounds with bases or acids.

(6) The polymers derived from the N-carboxyalkylation of chitosan such as N-carboxymethyl chitosan or N-carboxybutyl chitosan sold under the name "EVALSAN" by the company JAN DEKKER.

(7) The polymers corresponding to the general formula (XVI) as described for example in French Pat. No. 1,400,366:

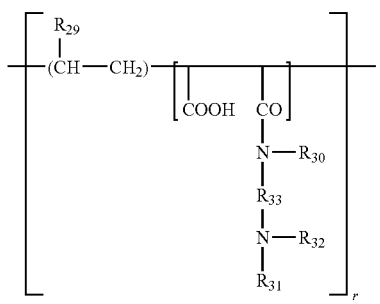

wherein $R_{29}$ is chosen from hydrogen atoms, $CH_3O$, $CH_3CH_2O$ and phenyl radicals, $R_{30}$ is chosen from hydrogen atoms and lower alkyl radicals such as methyl or ethyl, $R_{31}$ is chosen from hydrogen atoms and lower alkyl radicals such as methyl or ethyl, $R_{32}$ is chosen from lower alkyl radicals such as methyl or ethyl and radicals corresponding to the formula: $—R_{33}—N(R_{31})_2$, wherein R33 is chosen from $—CH_2—CH_2—$, $—CH_2—CH_2—CH_2—$ and $—CH_2—CH(CH_3)—$ groups, $R_{31}$ having the meanings mentioned above, and r is a number greater than 1. and also the higher homologues of these radicals and comprising up to 6 carbon atoms.

(8) Amphoteric polymers of the -D-X-D-X— type chosen from:

a) the polymers obtained by the action of chloroacetic acid or sodium chloroacetate on the compounds comprising at least one unit of formula:

-D-X-D-X-D- (XVII)

where D is chosen from a radical

and X is chosen from the symbol E or E', E or E', which may be identical or different, are each chosen from bivalent radicals which are alkylene radicals with a linear or branched chain comprising up to 7 carbon atoms in the principal chain, which are unsubstituted or substituted with hydroxyl groups and which may comprise, in addition, oxygen, nitrogen or sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, or hydroxyl, benzylamine, amine oxide, quaternary ammonium, amide, imide, alcohol, ester and/or urethane groups;

b) the polymers of formula:

-D-X-D-X— (XVIII)

wherein D is a radical

and X is chosen from E and E' and at least once, E'; E having the meaning indicated above and E' is a bivalent radical which is an alkylene radical with a linear or branched chain having up to 7 carbon atoms in the principal chain, which is unsubstituted or substituted with at least one hydroxyl radical and comprising at least one nitrogen atom, the nitrogen atom being substituted with an alkyl chain optionally interrupted by an oxygen atom and necessarily comprising at least one carboxyl functional group or at least one hydroxyl functional group and betainized by reaction with chloroacetic acid or sodium chloroacetate.

(9) The copolymers $(C_1-C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also comprise other vinyl comonomers such as vinylcaprolactam.

In one embodiment, the amphoteric polymers used are those of family (1).

In at least one embodiment, the at least one cationic or amphoteric substantive polymer, are present in an amount ranging from 0.01% to 10% by weight relative to the total weight of the composition, for example, from 0.05% to 5% by weight, such as from 0.1% to 3% by weight, relative to the total weight of the composition.

The appropriate medium for dyeing keratin fibers used herein comprises water or a mixture of water and at least one organic solvent to solubilize the compounds which might not be sufficiently soluble in water. By way of organic solvent, there may for example be mentioned lower $C_1$-$C_4$ alkanols such as ethanol and isopropanol; polyols and polyol ethers such as 2-butoxyethyl, propylene glycol, propylene glycol monomethyl ether, diethylene glycol monoethyl ether and monomethyl ether, and aromatic alcohols such as benzyl alcohol or phenoxyethanol, and mixtures thereof.

The solvents may be present in amounts ranging from 1% to 40% by weight, for example, from 5% to 30% by weight, relative to the total weight of the composition.

The composition may also comprise customary additives in the field such as organic or inorganic thickeners; antioxidants; penetrating agents; sequestering agents; perfumes; buffers; dispersing agents; conditioners different from the cationic or amphoteric substantive polymers such as for example cations, modified or unmodified, volatile or nonvolatile silicones; film-forming agents; ceramides; preservatives; stabilizers; opacifying agents.

Persons skilled in the art will be careful to choose this or these optional additional compounds such that the advantageous properties intrinsically attached to the composition disclosed herein are not, or not substantially impaired by the addition(s) envisaged.

Also disclosed herein is a process for dyeing keratin materials using the composition disclosed herein.

According to one embodiment, the process comprises applying the composition in the absence of an oxidizing agent to keratin materials, for example, fibers, dry or wet, with or without final rinsing of the composition.

In the case of this embodiment, the composition disclosed herein does not comprise an oxidation dye precursor, but only at least one direct dye.

In another embodiment, the process comprises applying the composition disclosed herein, in the presence of an oxidizing agent, to the keratin materials, dry or wet, and then in leaving in for a sufficient period to obtain the desired color.

According to another embodiment, at least one dye composition disclosed herein and an oxidizing composition are applied to said keratin fibers simultaneously or successively without intermediate rinsing.

In at least one embodiment, the composition applied is a "ready-to-use composition," that is to say a composition obtained by freshly mixing at least one dye composition disclosed herein with a composition comprising at least one oxidizing agent.

In this case, the dye composition may comprise at least one oxidation dye precursor. It may also comprise at least one direct dye, in the case where lightening of the keratin fibers is desired in combination with the coloration.

For example, the dye composition may comprise a combination of oxidation dye precursors and direct dyes.

The oxidizing agent present in the oxidizing composition may be chosen for example from hydrogen peroxide, urea peroxide, alkali metal bromates, persalts such as perborates and persulphates, and enzymes such as peroxydases or oxidoreductases comprising two or four electrons. In one embodiment, the oxidizing agent is hydrogen peroxide.

The oxidizing agent may be present in an amount ranging from 1% to 40% by weight, relative to the total weight of the ready-to-use composition, for example, from 1% to 20% by weight, relative to the total weight of the ready-to-use composition.

In one embodiment, the oxidizing composition used is an aqueous composition and is in the form of a solution or of an emulsion.

In another embodiment, the composition is mixed, free of oxidizing agent, with 0.5 to 10 equivalents by weight of the oxidizing composition.

It should be noted that the pH of the ready-to-use composition may range, for example, from 3 to 12, for example, from 4 to 11 and further, for example, from 6.5 to 10.5.

The pH of the ready-to-use composition may be adjusted by means of an alkalinizing or acidifying agent chosen, for example, from those mentioned above.

Where the composition is applied in the presence of an oxidizing agent, for example, the process may comprise a preliminary step comprising separately storing the at least one dye composition disclosed herein and a composition comprising at least one oxidizing agent in a medium that is suitable for dyeing human keratin fibers, and then mixing them together at the time of use, before applying this mixture to the wet or dry keratin materials.

Regardless of the presence or absence of oxidizing agent, the time required to develop the coloration ranges from a few seconds to 60 minutes, for example, from 1 to 50 minutes.

The temperature required to develop the coloration ranges from room temperature (15 to 25° C.) to 250° C., for example, from room temperature to 180° C. and further, for example, from room temperature to 60° C.

Once the time required to develop the coloration has elapsed, the composition may be, in at least some embodiments, removed.

Removal may take place in a conventional manner, either by carrying out at least one rinse, or by carrying out at least one washes and rinses, or by carrying out a combination thereof. Finally, the keratin materials may be dried or are left to dry.

Other than in the examples, or where otherwise disclosed, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently comprises certain errors necessarily resulting from the standard deviation found in their respective testing measurements.

The embodiments disclosed herein are illustrated in greater detail by the non-limiting example described below.

EXAMPLE

The following alkaline dye composition A was prepared (quantities expressed in grams):

|  | A composition |
|---|---|
| Oleic acid | 2 |
| Pure monoethanolamine | 0.47 |

-continued

|  | A composition |
|---|---|
| Oxyethylenated oleocetyl alcohol (30 EO) | 3.15 |
| Oxyethylenated lauryl alcohol (12 EO) | 4.4 |
| Oxyethylenated decyl alcohol (5 EO) | 3.15 |
| Oxyethylenated decyl alcohol (3 EO) | 12 |
| Oleyl alcohol | 1.8 |
| Monoisopropanolamide of copra acids | 4 |
| Alkylated (C14/16) hydroxyethylcellulose sold under the trade name Natrosol plus grade 330 CS; company Aqualon | 0.3 |
| Hydroxyethylcellulose quaternized with substituted lauryldimethylammonium epoxide (Polyquaternium-24) sold under the trade name Quatrisoft LM 200; company Amerchol | 0.15 |
| Glycerol | 3 |
| Nonstabilized polydimethyldiallylammonium chloride in water at 40% (Polyquaternium-6) | 3 |
| Ascorbic acid | 0.25 |
| EDTA | 0.2 |
| Ammonium thiolactate in aqueous solution at 58% | 0.8 |
| Aqueous ammonia (20% as ammonia) | 8 |
| 1-hydroxy-4-aminobenzene | 0.545 |
| 1-methyl-2-hydroxy-4-aminobenzene | 0.615 |
| Perfume | 0.95 |
| Deionized water | 51.22 |

The dye composition A was stable during storage.

The dye composition A was mixed, at the time of use, in a plastic bowl and for 2 minutes, with an aqueous oxidizing composition comprising 6% hydrogen peroxide, in an amount of 1 part of dye composition per 1.5 parts of oxidizing composition. The mixing was easy and rapid.

The mixture obtained was applied to locks of natural hair which were 90% white and was left in for 20 minutes. The application was easy and rapid. The product became perfectly localized, did not run, and spread well from the root to the end.

The locks were then rinsed with water, they were washed with standard shampoo, again rinsed with water and then dried and disentangled. The mixture was easy to remove on rinsing.

The hair was dyed in an intense red copper shade. Furthermore, the hair was not rough.

What is claimed is:

1. A dye composition comprising, in a medium appropriate for dyeing keratin fibers:
   at least one dye chosen from oxidation dye precursors and direct dyes;
   at least one surfactant chosen from nonionic and anionic surfactants;
   at least one fatty substance;
   at least one nonionic cellulose modified with at least one group chosen from saturated and unsaturated, linear and branched $C_6$-$C_{30}$ hydrocarbon chains; and
   at least one cationic associative polymer;
   wherein the dye composition comprises water in an amount greater than or equal to 40% by weight, relative to the total weight of the composition; and
   wherein the surfactant/fatty substance weight ratio is greater than 1.75.

2. A dye composition according to claim 1, wherein the dye composition comprises water in an amount greater than or equal to 45% by weight, relative to the total weight of the composition.

3. A dye composition according to claim 1, wherein the dye composition comprises water in an amount greater than or equal to 50% by weight, relative to the total weight of the composition.

4. A dye composition according to claim 1, wherein the at least one nonionic surfactant is chosen from:
   oxyalkylenated and glycerolated fatty alcohols;
   oxyalkylenated alkylphenols whose alkyl chain is $C_8$-$C_{18}$;
   oxyalkylenated and glycerolated fatty amides;
   oxyalkylenated vegetable oils;
   optionally oxyalkylenated fatty acid esters of sorbitan;
   optionally oxyalkylenated fatty acid esters of sucrose;
   fatty acid esters of polyethylene glycol;
   ($C_6$-$C_{30}$)alkyl polyglycosides;
   N-($C_6$-$C_{30}$)alkylglucamine derivatives;
   amine oxides; and
   copolymers of propylene and ethylene oxide.

5. A dye composition according to claim 4, wherein the at least one amine oxide is chosen from ($C_{10}$-$C_{14}$)alkylamine oxides and N-acylaminopropylmorpholine oxides.

6. A dye composition according to claim 1, wherein the at least one nonionic surfactant is chosen from oxyalkylenated fatty alcohols and glycerolated fatty alcohols.

7. A dye composition according to claim 1, wherein the at least one anionic surfactant is chosen from:
   ($C_6$-$C_{30}$)alkyl sulphates, ($C_6$-$C_{30}$)alkyl ether sulphates, ($C_6$-$C_{30}$)alkyl amidoether sulphates, alkyl aryl polyether sulphates, monoglyceride sulphates;
   ($C_6$-$C_{30}$)alkyl sulphonates, ($C_6$-$C_{30}$)alkyl amide sulphonates, ($C_6$-$C_{30}$)alkyl aryl sulphonates, α-olefin sulphonates, paraffin sulphonates;
   ($C_6$-$C_{30}$)alkyl phosphates;
   ($C_6$-$C_{30}$)alkyl sulphosuccinates, ($C_6$-$C_{30}$)alkyl ether sulphosuccinates, ($C_6$-$C_{30}$)alkyl amide sulphosuccinates;
   ($_6$-$C_{30}$)alkyl sulphoacetates;
   ($_6$-$C_{24}$)acyl sarcosinates;
   ($C_6$-$C_{24}$)acyl glutamates;
   ($C_6$-$C_{30}$)alkyl polyglycoside carboxylic ethers; ($C_6$-$C_{30}$) alkyl polyglycoside sulphosuccinates;
   ($C_6$-$C_{30}$)alkyl sulphosuccinamates;
   ($C_6$-$C_{24}$)acyl isethionates;
   N-($C_6$-$C_{24}$)acyltaurates;
   salts of $C_6$-$C_{30}$ fatty acids;
   ($C_8$-$C_{20}$)acyl lactylates;
   salts of ($C_6$-$C_{30}$)alkyl D-galactoside uronic acids; and
   salts of polyoxyalkylenated ($C_6$-$C_{30}$)alkyl ether carboxylic acids, of polyoxyalkylenated ($C_6$-$C_{30}$)alkyl aryl ether carboxylic acids and of polyoxyalkylenated ($C_6$-$C_{30}$) alkyl amidoether carboxylic acids.

8. A dye composition according to claim 1, wherein the at least one surfactant chosen from nonionic surfactants and anionic surfactants is present in an amount ranging from 0.01% to 40% by weight, relative to the total weight of the composition.

9. A dye composition according to claim 1, wherein the at least one modified nonionic cellulose is chosen from hydroxy ($C_2$-$C_3$)alkylcelluloses comprising at least one saturated or unsaturated, linear or branched $C_6$-$C_{30}$ hydrocarbon chain.

10. A dye composition according to claim 1, wherein the at least one modified nonionic cellulose is present in an amount ranging from 0.01% to 5% by weight, relative to the total weight of the composition.

11. A dye composition according to claim 1, wherein the at least one cationic associative polymer is chosen from quaternized cellulose derivatives, cationic polyurethanes, cationic polyvinyllactams and cationic acrylic terpolymers.

12. A dye composition according to claim 1, wherein the at least one cationic associative polymer is present in an amount ranging from 0.01 to 5% by weight, relative to the weight of the composition.

13. A dye composition according to claim 1, wherein the at least one oxidation dye precursor is chosen from oxidation bases and couplers.

14. A dye composition according to claim 13, wherein the at least one oxidation base is present in an amount ranging from 0.0005 to 12% by weight, relative to the total weight of the composition.

15. A dye composition according to claim 13, wherein the at least one coupler is present in an amount ranging from 0.0001 to 15% by weight, relative to the total weight of the composition.

16. A dye composition according to claim 1, wherein the at least one direct dye is present in an amount ranging from 0.0005 to 15% by weight, relative to the total weight of the composition.

17. A dye composition according to claim 1, wherein the composition further comprises at least one substantive polymer chosen from cationic and amphoteric substantive polymers.

18. A dye composition according to claim 17, wherein the at least one substantive polymer chosen from cationic and amphoteric substantive polymers is present in an amount ranging from 0.01% to 10% by weight, relative to the total weight of the composition.

19. A dye composition according to claim 1, wherein the composition further comprises at least one alkalinizing agent.

20. A dye composition according to claim 19, wherein the at least one alkalinizing agent is chosen from aqueous ammonia, alkanolamines and combinations of $C_2$-$C_{10}$ alkanolamines with alkali metal or alkaline-earth metal silicates.

21. A dye composition according to claim 1, wherein the at least one fatty substance is chosen from fatty alcohols, fatty acid amides, mono- and polyesters of carboxylic acids, mineral oils, and vegetable oils.

22. A dye composition according to claim 1, wherein the at least one fatty substance is present in an amount of less than or equal to 10% by weight, relative to the total weight of the composition.

23. A dye composition according to claim 1, wherein the composition further comprises at least one oxidizing agent.

24. A dye process for dyeing keratin fibers, comprising
applying to wet or dry keratin fibers a dye composition comprising, in a medium that is suitable for dyeing keratin fibers:
at least one dye chosen from oxidation dye precursors and direct dyes;
at least one surfactant chosen from nonionic surfactants and anionic surfactants;
at least one fatty substance;
at least one nonionic cellulose modified with at least one group chosen from saturated and unsaturated, linear and branched $C_6$-$C_{30}$ hydrocarbon chains; and
at least one cationic associative polymer;
wherein the dye composition comprises water in an amount greater than or equal to 40% by weight, relative to the total weight of the composition; and
wherein the surfactant/fatty substance weight ratio is greater than 1.75.

25. A process for dyeing keratin fibers, comprising
applying to wet or dry fibers, a dye composition in the presence of at least one oxidizing composition comprising at least one oxidizing agent, wherein said oxidizing composition is applied simultaneously with or successively to the dye composition without intermediate rinsing,
said dye composition comprising, in a medium that is suitable for dyeing keratin fibers:
at least one dye chosen from oxidation dye precursors and direct dyes;
at least one surfactant chosen from nonionic surfactants and anionic surfactants;
at least one fatty substance;
at least one nonionic cellulose modified with at least one group chosen from a saturated and unsaturated, linear and branched $C_6$-$C_{30}$ hydrocarbon chains; and
at least one cationic associative polymer;
wherein the dye composition comprises water in an amount greater than or equal to 40% by weight, relative to the total weight of the composition; and
wherein the surfactant/fatty substance weight ratio is greater than 1.75;
leaving the mixture on the fibers, and
rinsing the fibers.

26. A process for dyeing keratin fibers, comprising
applying to said wet or dry keratin fibers, in the presence of at least one oxidizing composition comprising at least one oxidizing agent, a dye composition, wherein said at least one oxidizing agent is mixed with the dye composition before application,
said dye composition comprising, in a medium that is suitable for dyeing keratin fibers:
at least one dye chosen from oxidation dye precursors and direct dyes;
at least one surfactant chosen from nonionic surfactants and anionic surfactants;
at least one fatty substance:
at least one nonionic cellulose modified with at least one group chosen from saturated and unsaturated, linear and branched $C_6$-$C_{30}$ hydrocarbon chains; and
at least one cationic associative polymer;
wherein the dye composition comprises water in an amount greater than or equal to 40% by weight, relative to the total weight of the composition; and
wherein the surfactant/fatty substance weight ratio is greater than 1.75;
leaving the mixture on the fibers, and
rinsing the fibers.

27. A multicompartment kit for dyeing keratin fibers, comprising at least one first compartment comprising a dye composition comprising, in a medium that is suitable for dyeing keratin fibers:
at least one dye chosen from oxidation dye precursors and direct dyes;
at least one surfactant chosen from nonionic surfactants and anionic surfactants;
at least one fatty substance;
at least one nonionic cellulose modified with at least one group chosen from saturated and unsaturated, linear and branched $C_6$-$C_{30}$ hydrocarbon chains; and
at least one cationic associative polymer;
wherein the dye composition comprises water in an amount of at least 40% by weight, relative to the total weight of the composition; and
wherein the surfactant/fatty substance weight ratio is greater than 1.75, and
at least one second compartment comprising an oxidizing composition comprising at least one oxidizing agent.

* * * * *

UNITED STATES PATENT AND TRADEMARK OFFICE
CERTIFICATE OF CORRECTION

PATENT NO. : 7,569,078 B2
APPLICATION NO. : 11/394234
DATED : August 4, 2009
INVENTOR(S) : Frédéric Legrand Page 1 of 1

It is certified that error appears in the above-identified patent and that said Letters Patent is hereby corrected as shown below:

In the claims:

Claim 7, column 32, line 31, "$(_6\text{-}C_{30})$alkyl" should read --$(C_6\text{-}C_{30})$alkyl--.

Claim 7, column 32, line 32, "$(_6\text{-}C_{24})$acyl" should read --$(C_6\text{-}C_{24})$acyl--.

Claim 26, column 34, line 31, "substance:" should read --substance;--.

Signed and Sealed this

Twenty-second Day of September, 2009

David J. Kappos
*Director of the United States Patent and Trademark Office*